United States Patent
Sakamoto et al.

(10) Patent No.: US 12,377,195 B2
(45) Date of Patent: *Aug. 5, 2025

(54) NERVE REPAIR SCAFFOLDS HAVING HIGH MICROCHANNEL VOLUME AND METHODS FOR MAKING THE SAME

(71) Applicants: THE REGENTS OF THE UNIVERSITY OF MICHIGAN, Ann Arbor, MI (US); THE REGENTS OF THE UNIVERSITY OF CALIFORNIA, Oakland, CA (US); THE UNITED STATES OF AMERICA AS REPRESENTED BY THE DEPARTMENT OF VETERANS AFFAIRS, Washington, DC (US)

(72) Inventors: Jeffrey S. Sakamoto, Ann Arbor, MI (US); Dena Shahriari, Woodland Hills, CA (US); Mark H. Tuszynski, La Jolla, CA (US); Wendy Campana, La Jolla, CA (US); Yacov Koffler, San Diego, CA (US)

(73) Assignees: THE REGENTS OF THE UNIVERSITY OF MICHIGAN, Ann Arbor, MI (US); THE REGENTS OF THE UNIVERSITY OF CALIFORNIA, Oakland, CA (US); THE UNITED STATES OF AMERICA AS REPRESENTED BY THE DEPARTMENT OF VETERANS AFFAIR, Washington, DC (US)

( * ) Notice: Subject to any disclaimer, the term of this patent is extended or adjusted under 35 U.S.C. 154(b) by 650 days.

This patent is subject to a terminal disclaimer.

(21) Appl. No.: 17/382,786

(22) Filed: Jul. 22, 2021

(65) Prior Publication Data

US 2021/0353833 A1    Nov. 18, 2021

Related U.S. Application Data

(63) Continuation of application No. 16/545,855, filed on Aug. 20, 2019, now Pat. No. 11,110,207, which is a
(Continued)

(51) Int. Cl.
*A61L 27/56*    (2006.01)
*A61L 27/18*    (2006.01)
(Continued)

(52) U.S. Cl.
CPC ............... *A61L 27/56* (2013.01); *A61L 27/18* (2013.01); *A61L 27/34* (2013.01); *A61L 27/58* (2013.01);
(Continued)

(58) Field of Classification Search
CPC .......... A61L 27/56; A61L 27/18; A61L 27/34; A61L 27/58; A61L 27/54; A61L 2300/252; A61L 2300/412; A61L 2430/32
See application file for complete search history.

(56) References Cited

U.S. PATENT DOCUMENTS

| 6,716,225 B2 | 4/2004 | Li et al. |
| 8,075,904 B2 | 12/2011 | Sakamoto et al. |

(Continued)

FOREIGN PATENT DOCUMENTS

WO    WO-2006017845 A2    2/2006

OTHER PUBLICATIONS

International Search Report and Written Opinion issued in PCT/US2016/056104, mailed Jan. 17, 2017; ISA/KR.
(Continued)

*Primary Examiner* — Trevor Love
(74) *Attorney, Agent, or Firm* — FisherBroyles, LLP; Pedro F. Suarez

(57) ABSTRACT

Tissue scaffolds for neural tissue growth have a plurality of microchannels disposed within a sheath. Each microchannel comprises a porous wall having a thickness of ≤about 100 μm that is formed from a biocompatible and biodegradable material comprising a polyester polymer. The polyester polymer may be polycaprolactone, poly(lactic-co-glycolic acid) polymer, and combinations thereof. The tissue scaffolds have high open volume % enabling superior (linear and high fidelity) neural tissue growth, while minimizing inflammation near the site of implantation in vivo. In other aspects, methods of making such tissue scaffolds are provided. Such a method may include mixing a reduced particle size porogen with a polymeric precursor solution. The material is cast onto a template and then can be processed, including assembly in a sheath and removal of the porogen, to form a tissue scaffold having a plurality of porous microchannels.

23 Claims, 22 Drawing Sheets

Related U.S. Application Data continuation of application No. 15/765,981, filed as application No. PCT/US2016/056104 on Oct. 7, 2016, now Pat. No. 10,426,872.

(60) Provisional application No. 62/238,506, filed on Oct. 7, 2015.

(51) Int. Cl.
*A61L 27/34* (2006.01)
*A61L 27/54* (2006.01)
*A61L 27/58* (2006.01)

(52) U.S. Cl.
CPC ......... *A61L 27/54* (2013.01); *A61L 2300/252* (2013.01); *A61L 2300/412* (2013.01); *A61L 2430/32* (2013.01)

(56) References Cited

U.S. PATENT DOCUMENTS

| | | |
|---|---|---|
| 2007/0010831 A1 | 1/2007 | Romero-Ortega et al. |
| 2010/0047310 A1 | 2/2010 | Chen et al. |
| 2012/0221025 A1 | 8/2012 | Simpson et al. |
| 2014/0370094 A1 | 12/2014 | Wray et al. |
| 2018/0280580 A1 | 10/2018 | Sakamoto et al. |

OTHER PUBLICATIONS

Blesch, Armin et al., "Spinal cord injury: plasticity, regeneration and the challenge of translational drug development," *Trends in Neurosciences*, vol. 32, No. 1, pp. 41-47 (Published online Oct. 30, 2008); DOI: 10.1016/j.tins.2008.09.008.

Doyle, Heather et al., "Evaluation of a Multiscale Modelling Methodology to Predict the Mechanical Properties of PCL/β-TCP Sintered Scaffold Materials," *Annals of Biomedical Engineering* (2015), 43, pp. 1989 (Published online Dec. 2, 2014); DOI: 10.1007/s10439-014-1199-x.

Fairbairn, Neil G. et al., "Augmenting peripheral nerve regeneration using stem cells: A review of current opinion," *World J. Stem Cells*, 26, 7(1), pp. 11-26 (Published online Jan. 26, 2015); DOI: 10.4252/wjsc.v7.i1.11.

Grinsell, D. et al., "Peripheral Nerve Reconstruction after Injury: A Review of Clinical and Experimental Therapies," *BioMed Research International*, vol. 2014, 698256 (Published Sep. 3, 2014); DOI: 10.1155/2014/698256.

Hundepool, Caroline A. et al., "The effect of stem cells in bridging peripheral nerve defects: a meta-analysis," *J. Neurosurg*, 121, pp. 195-209 (Published online May 9, 2014); DOI: 10.3171/2014.4.JNS131260.

Kappos Elisabeth A. et al., "Peripheral Nerve Repair: Multimodal Comparison of the Long Term Regenerative Potential of Adipose Tissue Derived Cells in a Biodegradable Conduit," *Stem Cells and Development*, 24 (18), pp. 2127-2141 (Published Jul. 2, 2015); DOI: 10.1089/scd.2014.0424.

Kehoe, S. et al., "FDA approved guidance conduits and wraps for peripheral nerve injury: A review of materials and efficacy," *Injury, Int. J. Care Injured*, 43 (2012), pp. 553-572; DOI: 10.1016/j.injury.2010.12.030.

Konofaos, P. et al., "Nerve Repair by Means of Tubulization: Past, Present, Future," *J Reconstr Microsurg* (2013), 29, pp. 149-164 (Published online Jan. 9, 2013); DOI: 10.1055/s-0032-1333316.

Li, Ruijun et al., "Peripheral Nerve Injuries Treatment: A Systematic Review," *Cell Biochemistry and Biophysics*, vol. 68, No. 3, pp. 449-454 (Published online Sep. 14, 2013); DOI: 10.1007/s12013-013-9742-1 (Abstract Only).

Prabhakaran, Molamma P. et al., "Surface modified electrospun nanofibrous scaffolds for nerve tissue engineering." *Nanotechnology*, 19 (2008) 455102 (Published Oct. 8, 2008); DOI: 10.1088/0957-4484/19/45/455102.

Sabongi, Rodrigo Guerra et al., "Peripheral nerve regeneration with conduits: use of vein tubes," *Neural Regeneration Research* (2015), vol. 10, No. 4, pp. 529-533; DOI: 10.410/1673-5374.155428.

Thomas, Aline M. et al., "Channel density and porosity of degradable bridging scaffolds on axon growth after spinal injury," *Biomaterials*, 34 (2013) pp. 2213-2220 (Published online Jan. 2, 2013); DOI: 10.1016/j.biomaterials.2012.12.002.

U.S. Appl. No. 16/545,855, filed Aug. 20, 2019.
U.S. Appl. No. 15/765,981, filed Apr. 4, 2018.

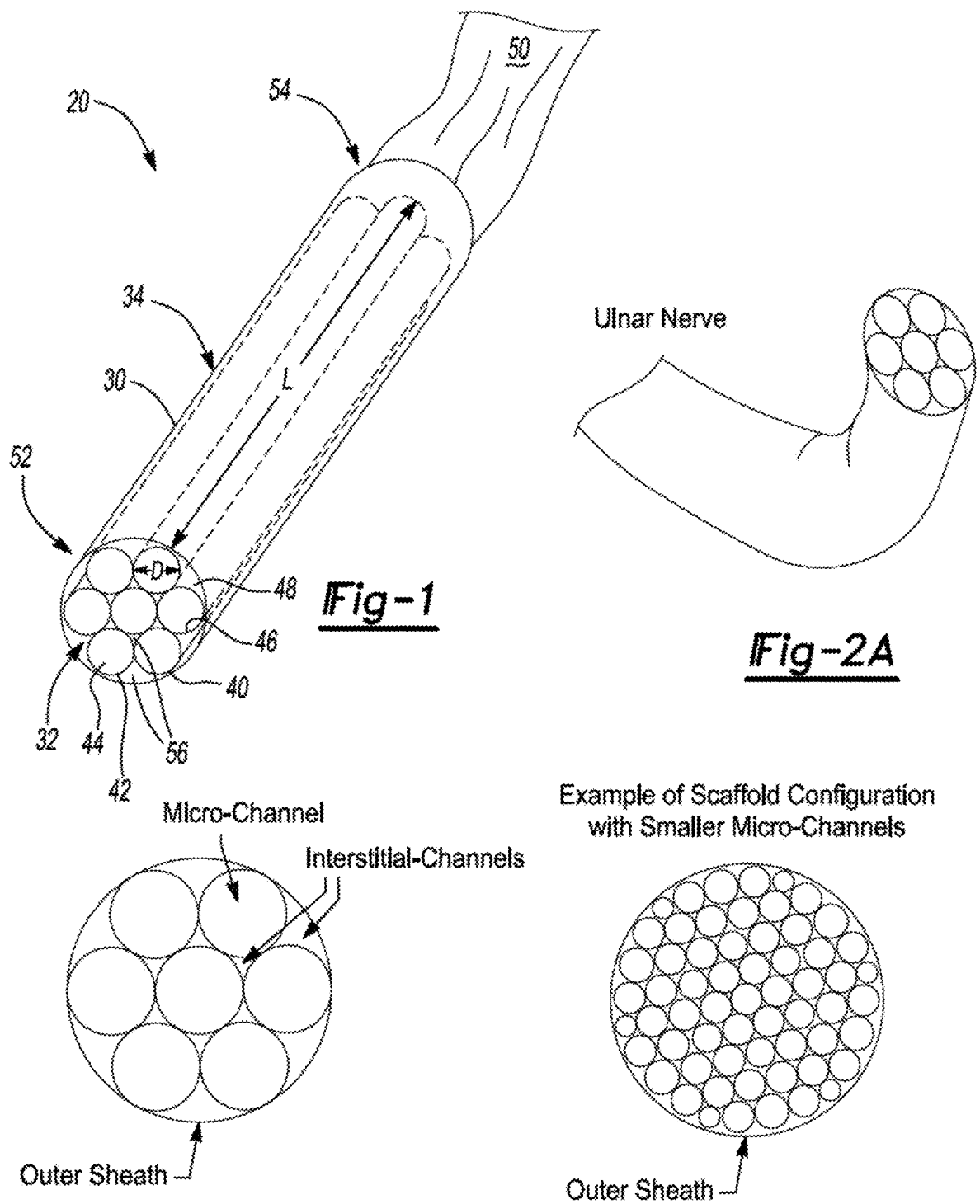

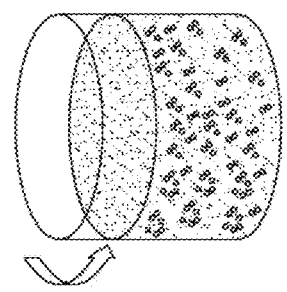
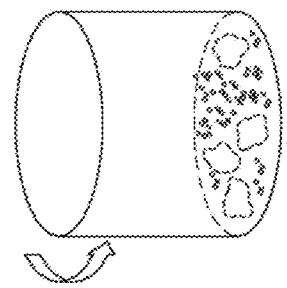
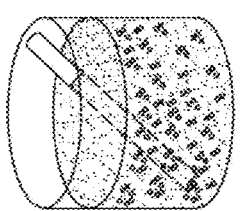
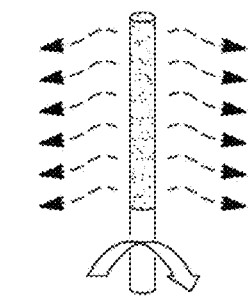
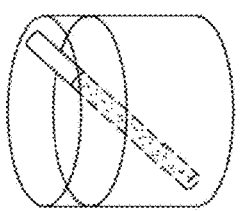
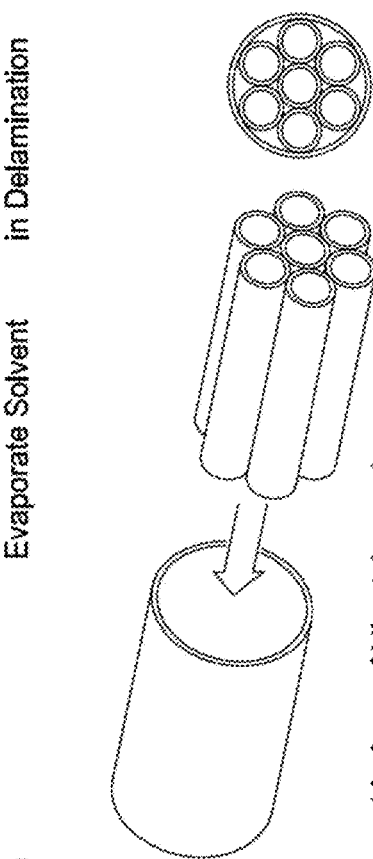
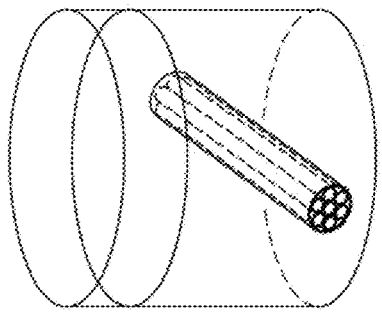
Fig-3

Cross-Section of 100% PCL Film:
Non-Porous

Cross-Section of 30 vol% PCL Film:
Interconnected Porosity

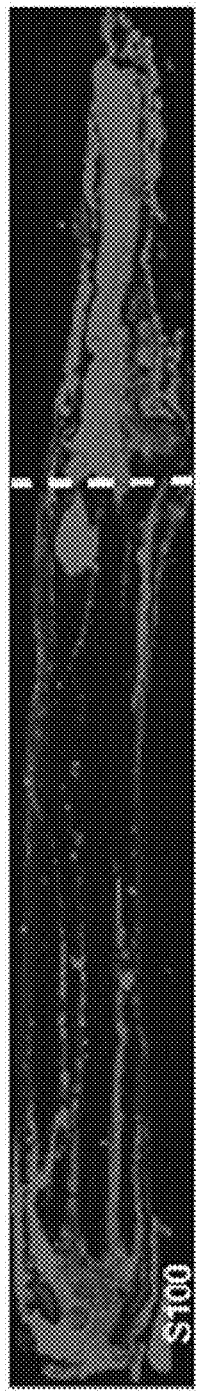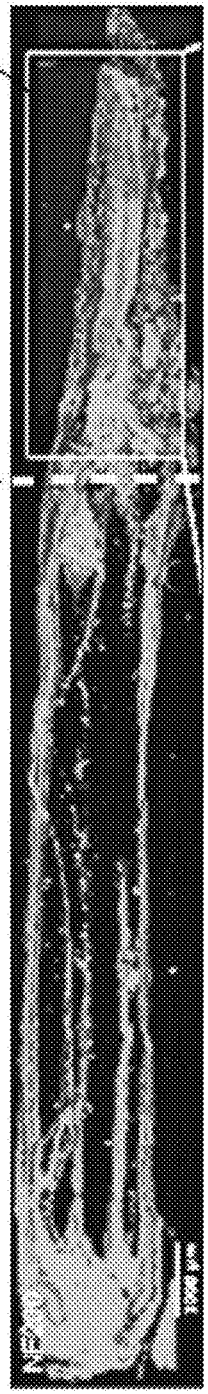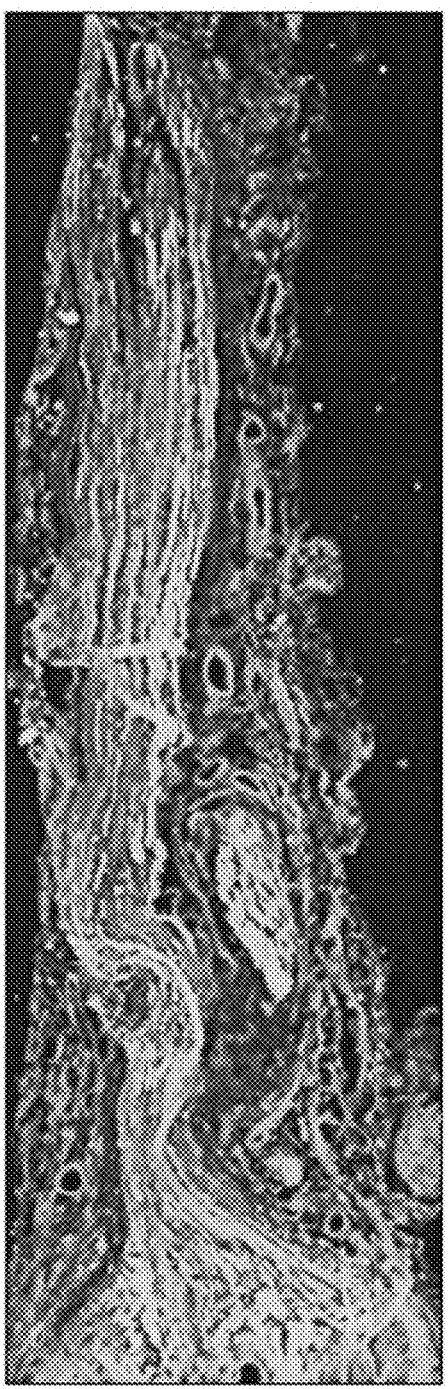
Fig-14A
Fig-14B
Fig-14C
4 Weeks Post Surgery Axons Reach 5.3mm into the Distal Nerve

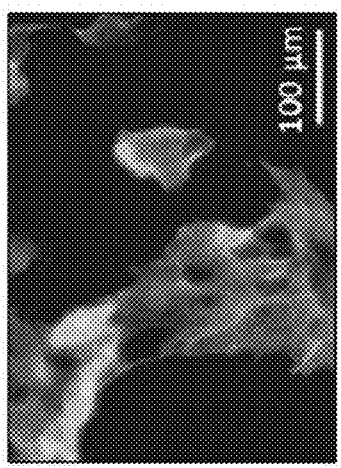
Fig-17A Positive Control-Well Plate
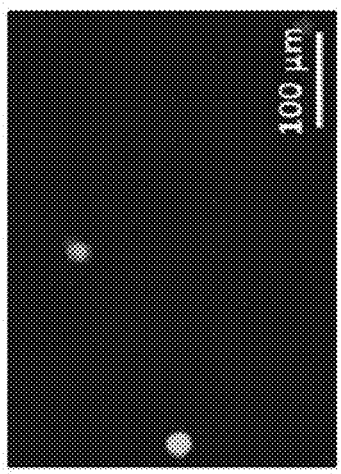
Fig-17B 100% Non-Porous PCL
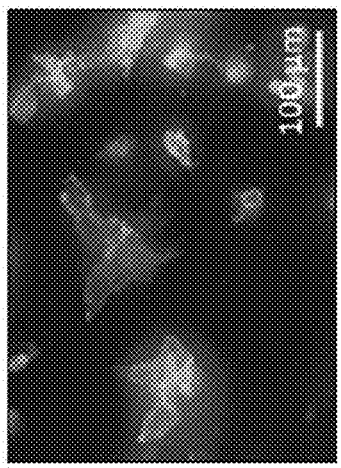
Fig-17C 30 vol% PCL
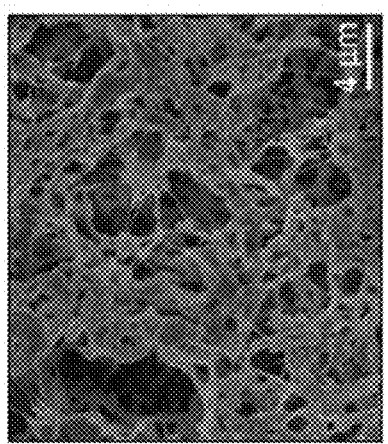
Fig-18A Surface of Inner Wall
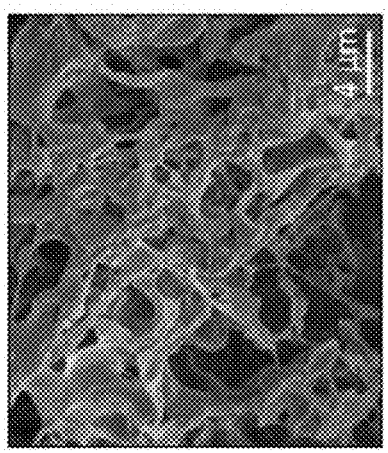
Fig-18B Cross-Section
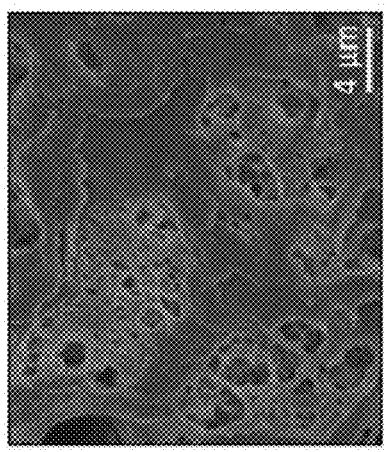
Fig-18C Outer Surface

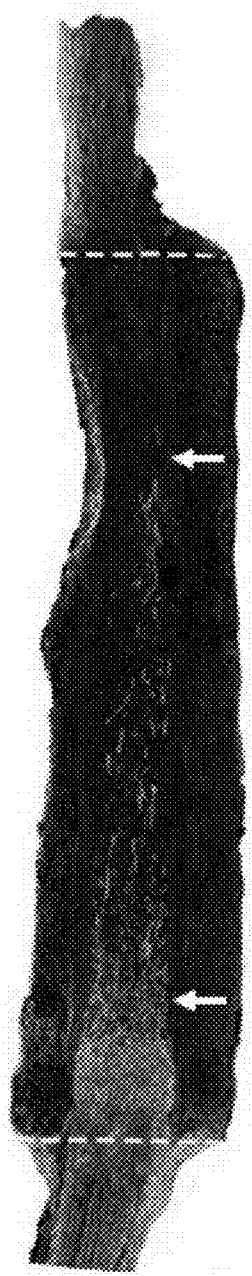 Fig-26A Neuragen
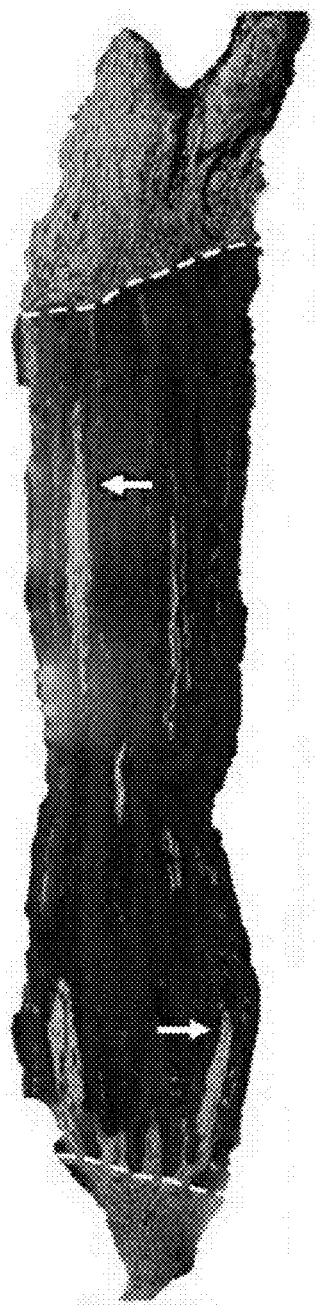 Fig-26B Microchannel Scaffold
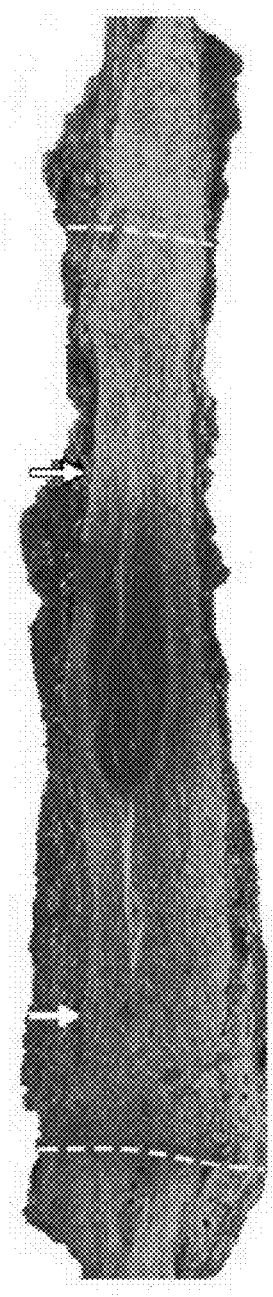 Fig-26C Autograft

NERVE REPAIR SCAFFOLDS HAVING HIGH MICROCHANNEL VOLUME AND METHODS FOR MAKING THE SAME

CROSS-REFERENCE TO RELATED APPLICATIONS

This application is a continuation of U.S. patent application Ser. No. 16/545,855, filed on Aug. 20, 2019, which is a continuation of U.S. patent application Ser. No. 15/765,981 filed on Apr. 4, 2018, which is a U.S. National Phase Application under 35 U.S.C. 371 of International Application No. PCT/US2016/056104 filed on Oct. 7, 2016 and published in English as WO 2017/062845 A1 on Apr. 13, 2017. This application also claims the benefit and priority of U.S. Application Ser. No. 62/238,506 filed on Oct. 7, 2015. The entire disclosures of the above applications are incorporated herein by reference.

GOVERNMENT SUPPORT

This invention was made with government support under EB014986 awarded by the National Institutes of Health. The Government has certain rights in the invention.

FIELD

The present disclosure relates to tissue scaffolds incorporating porous microchannels to promote neural tissue growth and methods for making such tissue scaffolds.

BACKGROUND

Although the peripheral nervous system (PNS) has a greater capacity for regeneration than the central nervous system (CNS), functional regeneration after injury is largely incomplete if injured axons become misaligned or lose contact with innervated tissues. Major functional deficits result and include deficient re-innervation of target tissues and painful neuroma formation.

Factors that influence PNS regeneration include the nature and the level of the damage itself, the period of denervation, the type and diameter of the damaged nerve fibers, and age. Proximal nerve injuries or complete transection of a large gap of the nerve generally have poorer outcomes with minimal clinically meaningful motor and sensory recovery. Several reasons contributing to suboptimal recovery have been identified and include: 1) deficiencies in rate of axonal regrowth; 2) compromise to an otherwise permissive environment for axonal elongation; 3) changes in the target tissue or path to reach the target tissue; 4) excessive and chronic neuroinflammation; and 5) Schwann cell (SC) atrophy and dysfunction.

Currently, the standard in clinical practice for surgical repair of peripheral nerve interface (PNI), in which there is a large gap in the peripheral nerve, involves placement of autologous nerve grafts. Disadvantages of autografts include: 1) donor site morbidity; 2) limited supply of donor grafts; and 3) increased time and complexity of surgery.

Experimental development of scaffolds to support peripheral nerve repair have resulted in commercially available nerve guides, but these scaffolds provide only single large diameter tubes that result in misalignment of regenerating axons with their proper targets. In one example, NEUROGEN™ sold by Integra LifeSciences is an open tube scaffold. Upon implantation with a transected rat sciatic nerve model, such an open tube scaffold shows that many axons undesirably lose linear orientation along a proximal end, only 200 µm after they enter the scaffold, prior to reaching the other distal end. Axons are less dense and of those that reach the distal end, some still lose orientation even as they exit into the distal nerve. This misguidance of axons can cause pain due to neuroma. Furthermore, such commercially available scaffolds lack seeding with growth-promoting substances, such as growth factors. Recently, cellular approaches including development of conduits filled with Schwann cells have shown some success because Schwann cells naturally support axonal regeneration by guiding and supporting axon growth, but these cells have not been translated for human peripheral nerve injury.

Moreover, there are no effective therapies for promoting regeneration after either acute or chronic spinal cord injuries (SCI) in humans. Various experimental approaches promote axonal regeneration in SCI animal models, including cell grafting to sites of injury to support axonal attachment and elongation. Grafted cells include astrocytes, Schwann cells, marrow stromal cells or stem cells. However, a drawback of cellular implants is a lack of 3D organization, resulting in random directions of axon growth; most axons do not regenerate beyond the injury site into host tissue, and hence functional recovery is extremely modest if present at all.

Thus, there remains a need to identify strategies and technologies for enhancing the extent, rate, guidance, targeting and lesion-distance over which neural tissue (e.g., axons) can regenerate.

SUMMARY

This section provides a general summary of the disclosure, and is not a comprehensive disclosure of its full scope or all of its features.

In certain aspects, the present disclosure provides new tissue scaffolds for neural tissue growth. In one aspect, the disclosure provides such a tissue scaffold that comprises a plurality of microchannels disposed within a sheath. Each microchannel comprises a porous wall having a thickness of less than or equal to about 100 µm. The porous wall comprises a biocompatible and biodegradable material comprising a polyester polymer. The polyester polymer may be selected from a group consisting of: polycaprolactone, poly (lactic-co-glycolic acid) polymer, and combinations thereof.

In other aspects, the present disclosure provides methods of making a tissue scaffold for promoting neural tissue growth. Such a method may comprise admixing a porogen with a polymeric precursor solution to form a suspension. The porogen has an average particle size of less than or equal to about 40 µm. The polymeric precursor solution comprises a biocompatible and biodegradable polyester polymer precursor and a first solvent. Then, a template is contacted with the suspension to coat at least one surface. At least a portion of the first solvent is volatized from the material on the template to form a coating. The coating is then removed from the template. The porous microchannel may be disposed or assembled inside a sheath with a plurality of other porous microchannels. Finally, the porogen may be removed to form a porous microchannel and thus, the tissue scaffold is formed having a plurality of porous microchannels arranged therein.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 shows a perspective view of an exemplary implantable tissue scaffold device having a plurality of porous microchannel tubes contained with a sheath according to certain aspects of the present disclosure.

FIGS. 2A-2C. FIG. 2A shows a picture of a cross-section of an ulnar nerve showing natural axonal architecture. FIGS. 2B-2C show cross-sectional schematics of two different high lumen volume nerve repair scaffolds which ideally match or emulate a nerve's native architecture according to certain aspects of the present disclosure. The design in FIG. 2C has a higher microchannel density than a microchannel density in FIG. 2B.

FIG. 3 shows a schematic of a scaffold fabrication process according to certain aspects of the present disclosure.

FIGS. 4A-4D. FIG. 4A shows a fabricated microchannel. FIG. 4B shows a fabricated outer sheath. FIG. 4C shows an assembly device with a custom claim shell slot die for assembling microchannels within a sheath. FIG. 4D shows the device inserting a microchannel array into an outer sheath.

FIGS. 5A-5C. FIGS. 5A-5C are pictures of a porogen salt-templated polycaprolactone (PCL) scaffold. FIG. 5A shows one terminal end of the scaffold, while FIG. 5B is a magnified view taken from the rectangle indicated in FIG. 5A showing the microchannels (having a scale bar of 500 µm). FIG. 5C is a side view of the tissue scaffold in FIGS. 5A-5B.

FIG. 6 shows a cross-sectional SEM image of a 30 vol. % PCL —70 vol. % NaCl porogen material before salt leaching (immersion in water to remove the porogen); fracture surface. An average NaCl particle size is about 17 µm prior to salt leaching.

FIGS. 7A-7B show SEM fracture surface images of PCL. FIG. 7A shows PCL without any porogen salt-templated that is therefore 100% dense. The scale bar is 2 µm. FIG. 7B shows porogen salt-templated PCL, exhibiting substantial porosity created by NaCl particles. The scale bar is 5 µm.

FIGS. 8A-8D. FIGS. 8A-8D are SEM images of porogen salt-templated PLGA 85/15. FIG. 8A shows 0% porosity (scale bar is 5 µm), FIG. 8B shows 40% porosity (scale bar is 20 µm), FIG. 8C shows 50% porosity (scale bar is 10 µm), and FIG. 8D shows 60% porosity (scale bar is 20 µm).

FIG. 9 shows Young's modulus of PCL as a function of PCL volume % (n=5 for each % porosity).

FIGS. 10A-10C. FIGS. 10A-10C show a hybrid micro-drilled agarose microchannel scaffold. FIG. 10A shows a terminal end view of the microchannel scaffold (scale bar is 300 µm) and FIG. 10B shows a side view of the microchannel scaffold (scale bar is 1 mm). A porogen salt-templated PCL sheath is shown in FIG. 10C (scale bar is 1 mm).

FIG. 11 is a photograph taken of an implanted hybrid PCL sheath and agarose scaffold (shown in FIGS. 10A-10C) after 8 weeks in vivo. The scaffold remains intact with no noticeable sign of inflammation.

FIGS. 12A-12B. After 8 weeks in vivo, the implanted hybrid sheath and scaffold (shown in FIGS. 10A-10C) show neurofilament growth (in green) and supporting neural cells (Schwann cells). As can be seen, robust axon and Schwann cell integration occurs and ingress (proximal) and egress (distal) is apparent from the agarose microchannels.

FIGS. 13A-13C. Tissue scaffolds have chitosan sheaths housing a micro-drilled agarose scaffold. FIG. 13A shows a picture of a chitosan sheath and agarose scaffold adjacent to a penny coin. The chitosan caused significant inflammation despite the use of low endotoxin grade chitosan. FIG. 13B is an optical image showing the agarose scaffold (linear features are the intact channels) is intact at the experiment completion. FIG. 13C shows Nissl staining demonstrating significant inflammation (yellow arrows) along the scaffold periphery.

FIGS. 14A-14C. FIGS. 14A-14C show tissue growth in a tissue scaffold having a PCL sheath and PCL microchannel scaffold according to certain aspects of the present disclosure implanted in a rat sciatic nerve 4 weeks post implantation (left side is proximal, right side is distal). FIG. 14A shows a cross-section stained with S100 to highlight Schwann cells. FIG. 14B shows a cross-section stained with NF200 to highlight neural tissue. FIG. 14C shows a magnified view of the distal end of FIG. 14B highlighting axons penetrating into host tissue after egress from the scaffold.

FIG. 15 shows a tissue scaffold having a PCL sheath and an array of PCL microchannels for use as a CNS scaffold. The scale bar is 300 micrometers.

FIG. 16 is a cross-section showing a CNS tissue scaffold having a PCL sheath and an array of PCL microchannels implanted in a rat T3 full transection. "W" and "C" are abbreviations for scaffold walls and channels respectively. NF200 stain highlights axons in white; yellow arrows point to regenerated axons. Scale bar is 500 micrometers.

FIGS. 17A-17C. FIGS. 17A-17C show cell attachment on a control and PCL materials for purposes of comparison. 3T3 fibroblast cells are stained for actin and nucleus. FIG. 17A shows a positive control of cell growth in a well plate. FIG. 17B shows cell growth on non-porous PCL (100% by volume PCL). FIG. 17C shows 3T3 fibroblast cell growth a porous PCL prepared in accordance with certain aspects of the present disclosure having 30 volume % PCL (70 volume % porosity). All scale bars are 100 µm.

FIGS. 18A-18C. FIGS. 18A-18C show that the walls of microchannels have interconnected porosity. FIG. 18A shows an SEM of the surface of the inner wall, FIG. 18B shows an SEM of the cross-section of the wall, and FIG. 18C the outer surface of the wall of the microchannel. All scale bars are 4 µm.

FIGS. 19A-19B. FIG. 19A is rat spinal cord tissue scaffold having over 85% open volume prepared according to certain aspects of the present disclosure (scale bar is 300 µm). FIG. 19B is a pig sciatic nerve scaffold having over 85% open volume prepared according to certain aspects of the present disclosure (scale bar is 4 mm).

FIGS. 20A-20E. FIG. 20A (including FIGS. 20A(1)-20A (4)) include stains showing scaffold performance in a rat transected sciatic nerve. FIGS. 20A(1)-20A(2) show distal and proximal ends of a multichannel 10 mm PCL scaffold prepared in accordance with certain aspects of the present disclosure in transected rat sciatic nerve, 4 weeks post implant. Axons are labeled in red using NEUROFILLAMENT™ 200. Arrow heads point where the proximal transected nerve stump is anastomosed to the scaffold. Full arrows point to linear axons in the channels on the proximal and distal parts of the scaffold as well as in the egress. FIGS. 20A(3)-20A(4) show a conventional scaffold (NEURAGEN™) at the same time frame in a transected rat sciatic nerve. The axons have loose orientation shortly after they enter the scaffold (full arrows and circle where axons are perpendicular to regeneration axis). The few that reach the distal side are not oriented even if they exit to the egress. The scale bars are 200 µm. FIG. 20B shows tissue growth in a 15 mm agarose scaffold loaded with BDNF secreting-marrow stromal cells with additional distal nerve injection of BDNF to attract regenerating axons to exit the scaffold into the distal nerve. FIG. 20C (including FIGS. 20C(1)-20C(2)) show proximal and distal ends with many myelinated axons bridges in BDNF treated animals. FIG. 20C(1) is red—NF200. FIG. 20C(2) is green—S100. FIG. 20D (including FIGS. 20D(1)-20D(2)) are SEMs of the channels showing many myelinated axons in the BDNF treatment, similar to the autograft as well as vascularization (asterisks). FIG. 20E shows quantification of axon density 12 mm within the scaffold indicating that in BDNF group axon density in channel core is similar to syngeneic nerve autografts. **$P<0.05$ (comparing scaffold group loaded with GFP-expressing cells to other groups).

FIGS. 21A-21C. FIG. 21A is a schematic of nerve stump apposed with the scaffold interface inside the overhang sheath. The epineurium is then sutured to the overhang (arrows). The sleeve can be seen in agarose hydrogel scaffold (FIG. 21B) and folded out (white arrow) in PCL scaffold (FIG. 21C).

FIGS. 22A-22B. FIG. 22A shows a schematic of porcine surgery site (arrow indicating surgical site). FIG. 22B shows a 15 mm scaffold, fabricated with PCL, implanted in transected porcine sciatic nerve. White arrows point to the suture where the scaffold is anastomosed with the epineurium of the nerve stumps.

FIGS. 23A-23D. FIGS. 23A-23D show a scaffold 3 months post implantation in for a transected pig sciatic nerve site. FIG. 23A shows a site overview in a horizontal plane. Many Schwann cells (S100-red) are evident on the proximal side. Scale is 2 mm. FIGS. 23B-23C have axon labeling (NF200-green) showing axonal penetration into the scaffold on the proximal side. These reach the distal side of the scaffold in a linear fashion. White arrows point to the channel, scale is 100 µm. FIG. 23D shows that associated axons and Schwann cells are observed in the distal stump, 4 mm beyond the distal end of the scaffold. Scale is 20 µm.

FIGS. 24A-24C. FIG. 24A (including FIGS. 24A(1)-24A(3)) shows a skin sensory test just after sciatic nerve transection in a pig. FIG. 24B (including FIGS. 24B(1)-24B(2)) shows preliminary results 3 months post scaffold implant. FIG. 24C shows the area on the skin is innervated by the Common fibular nerve—a branch of the sciatic nerve.

FIGS. 25A-25C. FIG. 25A is a schematic of the anatomical structures present in a representative peripheral nerve structure. FIG. 25B shows a cross-sectional view of a terminal end of a micro-scaffold prepared in accordance with certain aspects of the present disclosure designed to mimic the natural architecture of a peripheral neve. FIG. 25C shows commercially available, Federal Drug Administration (FDA)-approved hollow tube scaffold devices from left to right: NEURAGEN™ nerve guide available from Integra Lifesciences Corp., NEUROTUBE™ available from Synovis Microcompanies Alliance, and NEUROLAC™ available from Polyganics.

FIGS. 26A-26C. FIGS. 26A-26C show comparative nerve guide implants in a rat transected sciatic nerve, 4 weeks post implantation. The axons are stained with Green-NF200. FIG. 26A shows the commercially available NEURAGEN™ nerve guide. FIG. 26B shows a microchannel scaffold device prepared in accordance with certain aspects of the present disclosure. FIG. 26C shows an autograft. The interrupted lines demarcate the implant-nerve interface. The arrows on the left point to the proximal side of the implant, while the arrows on the right point to the distal aspect of the implant.

FIG. 27 shows high magnification view of different areas from FIGS. 26A-26C of the implanted comparative nerve guide devices (NEURAGEN™ nerve guide, a microchannel scaffold device prepared in accordance with certain aspects of the present disclosure, and an autograft) for a rat transected sciatic nerve, 4 weeks post implantation. Views of stained axon growth are shown at the nerve stump, proximal scaffold, mid-scaffold, distal scaffold, distal nerve, and end of block. Scale Bar: 100 µm.

Figure 30A:
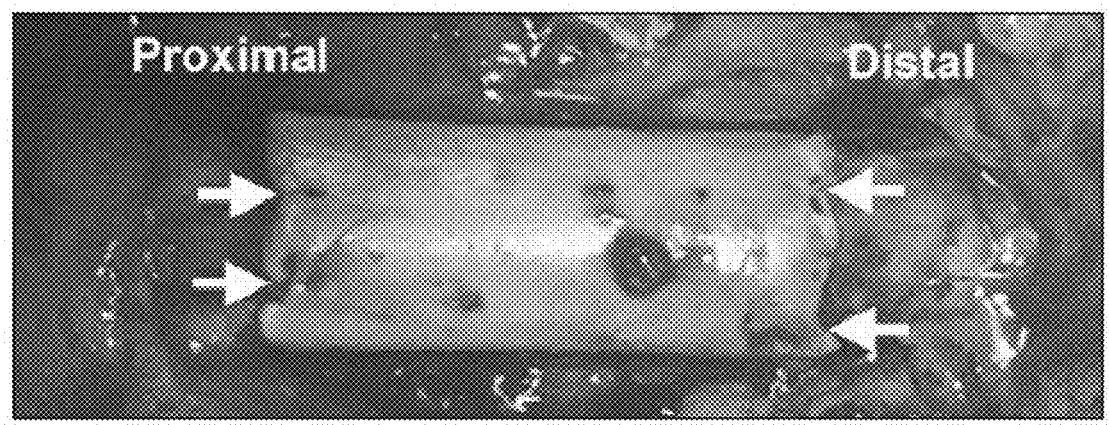

FIGS. 30A-30D. A microchannel scaffold device prepared in accordance with certain aspects of the present disclosure is shown implanted in pig transected sciatic nerve, 4 months post-surgery. FIG. 30A shows a 15 mm device, fabricated with PCL, implanted in transected porcine sciatic nerve. Arrows point to a suture where the device is anastomosed with the epineurium of the nerve stumps.

Figure 30B:
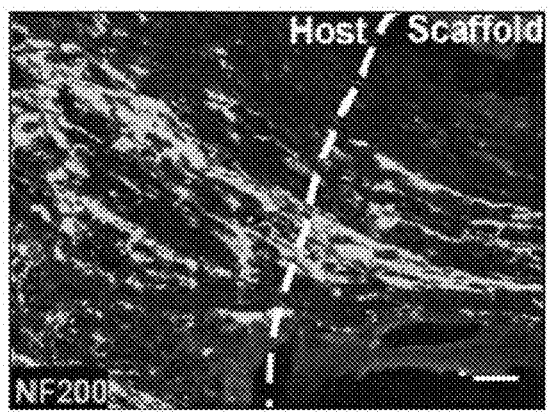
Figure 30C:
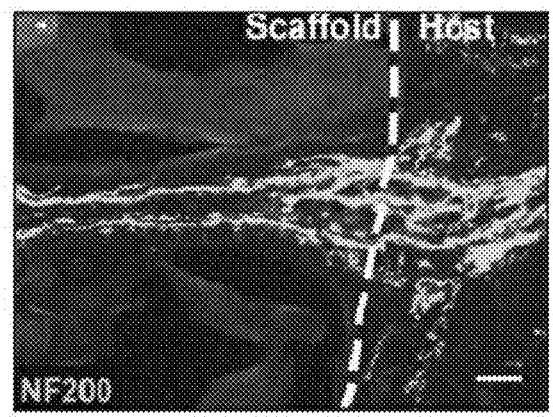
Figure 30D:
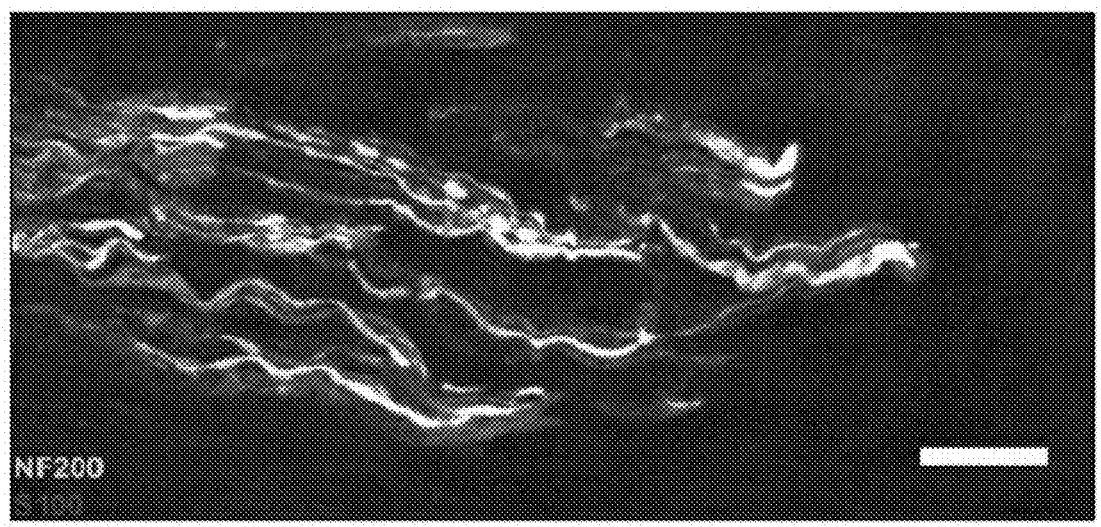

FIGS. 30B and 30C show axon labeling with NF200-green. FIG. 30B shows axonal penetration into the device on the proximal side, while FIG. 30C shows axons reaching the distal side of the device in a linear fashion. The interrupted line demarcates host-scaffold interface. FIG. 30D shows associated axons and Schwann cells observed in the distal stump, 3.5 mm beyond the distal end of the device. Scale in FIGS. 30B-30C: 50 micrometers.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Following severe trauma, the nervous system does not spontaneously regenerate, requiring intervention to restore function. There is a need to develop materials that enable the fabrication and implementation of improved and more effective nerve guidance scaffolds. In various aspects, the present disclosure contemplates an improved and more effective tissue scaffold for promoting neural tissue growth and proliferation in a subject. The subject may be an animal with a complex nerve system, such as a mammal, like a human, primate, or companion animal. The tissue scaffolds according to the present disclosure may thus be devices implanted in such a subject. As shown in FIG. 1, a tissue scaffold 20 includes a sheath 30. Inside the sheath 30, a plurality of microchannels 40 are disposed. Each microchannel in FIG. 1 thus includes a wall 42 and an open central lumen 44.

By "channel" it is meant that the structure defines an evident longitudinal axis and has an open lumen or hollow core. Channels having such an evident longitudinal axis include an elongated axial dimension, which is longer than the other dimensions (e.g., diameter or width) of the channel. Thus, the elongated channels are linear. In certain aspects, such elongated channel has an aspect ratio (AR) defined as a length of the longest axis divided by diameter of the component, which is preferably at least about 100 and in certain aspects greater than about 1,000. In yet other aspects, such channels may have an aspect ratio of 10,000 or more.

The present disclosure thus contemplates a scaffold 20 comprising a plurality of microchannels 40 respectively defining a longitudinal major axis "L" as shown in FIG. 1. The term "micro-sized" or "micrometer-sized" as used herein is generally understood by those of skill in the art to mean less than about 500 micrometers (μm) (i.e., 0.5 mm). In accordance with certain variations of the present disclosure, a "microchannel" preferably has at least one spatial dimension that is less than about 1,000 μm. In certain aspects, each microchannel has an inner diameter of greater than or equal to about 10 µm to less than or equal to about 1,000 µm, optionally greater than or equal to about 10 µm to less than or equal to about 500 µm, optionally greater than or equal to about 50 µm to less than or equal to about 450 µm, optionally greater than or equal to about 50 µm to less than or equal to about 300 µm. It should be noted that so long as at least one dimension of the microchannel falls within the above-described micro-sized scale (for example, diameter), one or more other axes may well exceed the micro-size (for example, length and/or width). For example, depending on the application, microchannels in accordance with certain variations of the present disclosure may have a length of greater than or equal to about 500 µm to less than or equal to 30 cm, optionally greater than or equal to about 500 µm to less than or equal to about 10 cm, and in certain variations, optionally greater than or equal to about 500 µm to less than or equal to about 3 cm, by way of non-limiting example.

The microchannels are formed of a biocompatible and biodegradable material, such as a biocompatible polymer. By "biocompatible," it is meant that a material or combination of materials can be contacted with cells, tissue in vitro or in vivo, or used with mammals or other organisms and has acceptable toxicological properties for contact and/or beneficial use with such cells, tissue, and/or animals. For example, a biocompatible material may be one that is suitable for implantation into a subject without adverse consequences, for example, without substantial toxicity or acute or chronic inflammatory response and/or acute rejection of the material by the immune system, for instance, via a T-cell response. It will be recognized that "biocompatibility" is a relative term, and some degree of inflammatory and/or immune response is to be expected even for materials that are highly compatible with living tissue. However, non-biocompatible materials are typically those materials that are highly toxic, inflammatory and/or are acutely rejected by the immune system, e.g., a non-biocompatible material implanted into a subject may provoke an immune response in the subject that is severe enough such that the rejection of the material by the immune system cannot be adequately controlled, in some cases even with the use of immunosuppressant drugs, and often can be of a degree such that the material must be removed from the subject. In certain aspects, biocompatible materials are those that are approved for use in humans by an appropriate regulatory agency, such as the Federal Drug Administration (FDA) in the United States; the European Commission (EC)/European Medicines Agency (EMEA) in Europe; or Health Products and Food Branch (HPFB) in Canada.

For example, a scaffold structure can comprise microchannels formed from biocompatible and biodegradable polymers, such as polyester polymers. Suitable biodegradable polymers for forming the microchannels include a polylactic acid, polycaprolactone (PCL), polyglycolic acid, poly(lactide-co-glycolide polymer (PLGA), and copolymers, derivatives, and mixtures thereof. In certain preferred aspects, the biocompatible and biodegradable material is selected the group of polymers consisting of: polycaprolactone (PCL), poly(lactic-co-glycolic acid) (PLGA), and combinations thereof.

In certain aspects, the polymers can also be modified by chemical or physical methods, such as cross-linking, heat treatment, photochemical treatment, and/or changes in the chemical or physical environment. In certain aspects, the polymer modification occurs in a select portion or region of one or more of the microchannels, or such polymer modification can occur to different degrees, potentially resulting in different materials or material responses, as appreciated by one of skill in the art. Such polymer modification and/or treatment provide different degradation or release kinetics in certain aspects. Further, surface alterations, such as differences in hydrophilicity, charge, or other physical properties, facilitate cell adhesion.

In certain aspects, the microchannels may be treated with a biofunctional agent or active ingredient; have different surface properties or surface roughness; or have surfaces with different moieties exposed, which can be useful in designing spatially guided cellular growth and in certain aspects to facilitate adhesion of cells or tissue or to promote release of biofunctional agents, which include biofunctional materials and active ingredients (e.g., pharmaceutical active ingredients), and the like, into the surrounding environment.

The biodegradable material forming the microchannel may dissolve, referring to physical disintegration, erosion, disruption and/or dissolution of a material and may include the resorption of such material by a living organism. In certain variations, biodegradable polymeric material may dissolve or erode upon exposure to a solvent comprising a high concentration of water, such as blood, serum, growth or culture media, bodily fluids, saliva, and the like. Thus, upon implantation, the material may dissolve or disintegrate into small pieces. For structural scaffold members, the dissolution rate (e.g., a rate at which the structural member is resorbed by surrounding cells) can be designed so that sufficient cellular growth occurs prior to the structure dissolving or disintegrating via the resorption process. In various embodiments, the tissue scaffold device is designed to have a degradation time or dissolution rate that coincides with an amount of time that permits adequate neural tissue regrowth through the scaffold to a target tissue in the subject. Depending upon the subject and the time needed for recuperation and regeneration of the tissue, by way of non-limiting example, the degradation time may be greater than or equal to about 1 month to less than or equal to about 3 years, greater than or equal to about 1 month to less than or equal to 1 year, and in certain variations, greater than or equal to about 1 month to less than or equal to 6 months. In this manner, the cellular scaffold structure supports and promotes cell growth, cell proliferation, cell differentiation, cell repair, and/or cell regeneration in three-dimensions, especially for neural tissue growth.

In certain aspects, the walls 42 of the microchannels 40 are porous. The pore size may be selected to promote substantially linear neural or axonal tissue growth along the longitudinal axis "L" while avoiding cell growth through and across the microchannel walls 42. In certain aspects, the walls 42 are highly porous, for example, having a porosity of greater than about 1% to less than or equal to about 99%, optionally having a porosity of greater than about 10% to less than or equal to about 95%. The plurality of pores within the walls 42 may include a plurality of internal pores and external pores that are open to one another and form continuous flow paths or channels through the wall 42 extending from a first internal surface 46 to a second external surface 48. As used herein, the terms "pore" and "pores" refer to pores of various sizes, including so-called "macropores" (pores greater than 50 nm diameter), "mesopores" (pores having diameter between 2 nm and 50 nm), and "micropores" (pores having diameter of less than 2 nm), where the pore size refers to an average or median value, including both the internal and external pore diameter sizes.

The walls 42 of the microchannels 40 optionally comprise a plurality of pores having an average pore size diameter of less than or equal to about 50 µm, optionally less than or equal to about 40 µm, optionally less than or equal to about 30 µm, optionally less than or equal to about 20 µm, and in certain variations, optionally less than or equal to about 10 µm. In certain aspects, the plurality of pores in the microchannel 40 wall 42 has an average pore size that eliminates line-of-sight pores that could allow axons to grow between respective microchannels 40. In certain other aspects, the average pore sizes in the walls 42 may be macropores ranging from greater than or equal to about 30 µm to less than or equal to about 50 µm. Such pore sizes promote flow of oxygen and nutrients through the walls 42 of the microchannel 40 from the external surface 48 to the internal surface 46 to support cells growing within the open central lumen 44, while minimizing or preventing cells from being able to grow through the microchannel walls 42. As will be discussed herein, techniques for making the scaffolds 20 introduce porosity and surface roughness at levels that promote cell adhesion to the microchannel 40 walls 42. In this manner, the scaffold 20 promotes cell growth, proliferation, differentiation, repair, and/or regeneration. In certain variations, the tissue is a neural tissue, such as axons.

Each microchannel 40 within the sheath 30 comprises a porous wall 42. In certain aspects, suitable wall 42 thicknesses are the smallest thicknesses possible that retain structural integrity to the channel. In certain aspects, the wall has a thickness of less than or equal to about 500 µm. In other aspects, the wall has a thickness of less than or equal to about 100 µm. Where wall thicknesses are greater than 100 µm, they can reduce the amount of space available within the open central lumen 44 for axonal regeneration. In certain variations, the wall thickness may be greater than or equal to about 10 µm to less than or equal to about 100 µm, optionally greater than or equal to about 10 µm to less than or equal to about 70 µm, optionally greater than or equal to about 20 µm to less than or equal to about 70 µm, optionally greater than or equal to about 25 µm to less than or equal to about 67 µm, and in certain aspects, optionally greater than or equal to about 20 µm to less than or equal to about 50 µm. In certain other variations, the wall has a thickness of greater than or equal to about 10 µm to less than or equal to about 20 µm.

One particular advantage of the tissue scaffold 20 design according to various aspects of the present disclosure is providing an overall open volume (e.g., open lumen volume, including the volume of open interstitial channels 56 within sheath 30 and open central lumen 44 of microchannels 40) of greater than or equal to about 50 volume %, optionally greater than or equal to about 60 volume %, optionally greater than or equal to about 70 volume %, optionally greater than or equal to about 80 volume %, and in certain preferred aspects, optionally greater than or equal to about 90 open volume % of the overall scaffold 20 volume. It should be noted that conventional scaffold designs were not able to achieve such high levels of open lumen volumes, which is believed to be particularly advantageous in supporting and promoting growth of healthy neural tissues having desirably high directional linearity and high signal fidelity.

In certain aspects, a diameter "D" of each microchannel 40 of the plurality of microchannels disposed within the sheath 30 is selected to be the same (or substantially the same accounting for small dimensional variances during manufacturing), although in alternative variations, the diameters D may intentionally vary between distinct microchannels 40 of the plurality present in the sheath (not shown in FIG. 1). As noted above, in variations where the plurality of microchannels 40 have substantially the same diameter, an average inner diameter D is optionally less than or equal to about 450 µm or any of the other ranges specified previously. Each microchannel 40 may have an oval or spherical cross-sectional shape to form microcylinder shapes that create significant open interstitial volumes in interstitial channels 56, although in alternative less preferred variations, other shapes may be used. Where the plurality of microchannels 40 has substantially the same diameters, they may be configured to be closely packed in an array within the sheath 30. Thus, a portion of each microchannel 40 contacts another adjacent microchannel 40. The plurality of microchannels 40 may be arranged within the sheath 30 in a close-packed array that may create a honeycomb type of arrangement. In this manner, the tissue scaffolds of the present disclosure comprise discrete, linear, thin-walled, close-packed arrays of microchannels 40 disposed within external protective sheath 30. A microchannel density may be varied in different embodiments, for example, the microchannel density may be greater than or equal to about 1 to less than or equal to about 300 microchannels/mm$^2$ in the scaffold. In certain variations, the microchannel density may be greater than or equal to about 10 to less than or equal to about 30 microchannels/mm$^2$. In another variation, the tissue scaffold may have a microchannel density of about 120 microchannels/mm$^2$.

The sheath 30 may be formed of a biocompatible and/or biodegradable material that may be the same as or different from the microchannels 40. Desirably, the sheath 30 may have a similar porosity to the microchannels 40 to promote flow and transport of nutrients to the microchannels, while minimizing or preventing cellular growth from an interior region 32 through the sheath to an exterior region 34. The sheath 30 is shown as a cylindrical tube shape with an oval or cylindrical cross-sectional shape; however, the sheath 30 may have a variety of other shapes, so long as the microcylinders can be arranged in an array within the sheath 30. Thus, in certain aspects, the sheath 30 may have other shapes, including a butterfly shape similar to that found in a human spinal column by way of non-limiting example. The sheath 30 may have a length that is the same as the microcylinders 40 or may be longer for additional protection and securing to a portion of a nerve 50 or surrounding tissue (e.g., by anastomosing). In this manner, the tissue scaffold 20, including the sheath 30 and microchannels 40 can extend over any distance to match injuries of individual subjects/patients.

The scaffold 20 can be filled with cells. These cells can be modified to express a growth factor or can be therapeutic in nature such as stem cells or Schwann cells.

A portion of nerve 50, such as a nerve end, of the subject may be damaged or severed, for example, a fully or partially lesioned nerve end caused by injury, disease, or surgery. In certain aspects, a portion of the nerve end may be surgically divided, sectioned, cut, and/or transected into one or more individual branches or fascicles that may be secured to a proximal end 52 or distal end 54 of the tissue scaffold 20. The one or more individual branches or fascicles of the nerve end 50 may contact or be placed within one or more microchannels 40. The nerve end (or its individual branches or fascicles) can be secured via sutures, adhesives, or other known securing techniques to the proximal or distal ends 52, 54 (shown in FIG. 1 as the distal end 54). Over a period of, for example, several months, the neural tissue originating from the nerve end 50 can grow along the longitudinal axis L of each microchannel 40 and reinnervate any neural targets at the opposite end of the tissue scaffold 20. The tissue scaffolds according to various aspects of the present teachings thus facilitate neural tissue growth through the open central lumens 44 of the plurality of microchannels 40 from a first end (e.g., proximal end 52) to a second opposite end of the (e.g., distal end 54) scaffold 20. As will be appreciated by those of skill in the art, while the design of the inventive tissue scaffolds is particularly suitable for promoting neural tissue growth, in alternative variations, the tissue scaffold may be used for other types of tissue growth.

In other aspects, surfaces of the walls 42 of microcylinders 40 may be coated with a biofunctional agent to promote cell growth, regeneration, differentiation, proliferation, and/or repair, for example. By "promoting" cell growth, cell proliferation, cell differentiation, cell repair, or cell regeneration, it is meant that a detectable increase occurs in either a rate or a measurable outcome of such processes occurs in the presence of the biofunctional agent as compared to a cell or organism's process in the absence of such a biofunctional agent, for example, conducting such processes naturally. By way of example, as appreciated by those of skill in the art promoting cell growth in the presence of a biofunctional agent may increase a growth rate of target cells or increase a total cell count of the target cells, when compared to cell growth or cell count of the target cells in the absence of such a biofunctional agent.

In certain variations, the biofunctional agent promotes cell growth, cell adhesion, cell proliferation, cell differentiation, cell repair, and/or cell regeneration by increasing a measurable process result (e.g., measuring total cell counts for cell generation or cell regeneration, measuring the rates or qualitative outcome of cell proliferation, cell differentiation, or cell repair rates) by greater than or equal to about 25% as compared to the result of the process in the absence of the biofunctional agent, optionally increasing by greater than or equal to about 30%, optionally increasing by greater than or equal to about 35%, optionally increasing by greater than or equal to about 40%, optionally increasing by greater than or equal to about 45%, optionally increasing by greater than or equal to about 50%, optionally increasing by greater than or equal to about 55%, optionally increasing by greater than or equal to about 60%, optionally increasing by greater than or equal to about 65%, optionally increasing by greater than or equal to about 70%, optionally increasing by greater than or equal to about 75%, optionally increasing by greater than or equal to about 80%, optionally increasing by greater than or equal to about 85%, optionally increasing by greater than or equal to about 90%, and in certain aspects, optionally increasing by greater than or equal to about 95%.

Such a biofunctional agent may be introduced after the microcylinders 40 are formed, for example, by coating, infusing, or otherwise incorporating the biofunctional agent onto one of more surfaces (e.g., internal surface 46) of the microchannel wall 42. In certain aspects, a surface of the porous wall 42 has a coating comprising a material for promoting growth of the neural tissue selected from the group consisting of: fibronectin, keratin, laminin, collagen, and combinations and equivalents thereof. In certain variations, the walls may be coated with fibronectin, which has been found after screening over a dozen compounds to be particularly advantageous with the biocompatible polymers forming the microchannel walls to optimize cell and axon attachment.

The present technology thus enables a major advance over existing technologies in surgical repair of injured peripheral nerves. There are currently seven FDA-approved devices on the market for peripheral nerve repair. However, all of these existing devices consist of only a single open channel (not divided into individual microchannels) in which axons frequently diverge from linear paths, reducing the number of axons that reach the distal end of the scaffold and contribute to nerve repair. Simpler designs like those commercially available more commonly result in painful neuromas because of axon misguidance. Additionally, the properties of materials out of which existing scaffolds have been fabricated do not adequately support cell and axon attachment. Furthermore, many of the materials out of which conventional tissue scaffolds have been made, including hydrogels, have shown significant and problematic inflammatory response. Based on empirical observation after implanting and testing hydrogel nerve regeneration scaffolds, hydrogel-based materials do not exhibit adequate strength to enable the fabrication of thin (<50 μm) wall scaffolds. Yet based on calculations, it appears that wall thicknesses of less than 50 microns are necessary to achieve >90% lumen volume scaffolds that adequately support and promote neural tissue growth. Thus, hydrogel based materials cannot provide scaffolds having adequate strength with advantageous open lumen volume provided by certain aspects of the present teachings.

The present tissue scaffold devices are superior in providing a multi-lumen design that enhances nerve guidance, thereby increasing the total number of axons that regenerate successfully. As a result, such tissue scaffold devices work over long nerve gaps and after more proximal nerve injuries, thereby addressing a great unmet medical need. Further, the tissue scaffolds according to the present disclosure are made from biocompatible and biodegradable materials, such as PCL and PLGA polymers, with optimized porosity and surface roughness, providing superior cell adhesion levels and directional cell growth while exhibiting significantly reduced inflammatory response in vivo after implantation. When tested in vivo, the devices of the present disclosure are biocompatible. Further, when directly compared side-to-side with current FDA-approved scaffolds for peripheral nerve repair, the inventive tissue scaffold design is superior: a greater number of axons are linearly organized and reach the distal end of the scaffold.

In this manner, the tissue scaffold devices according to certain aspects of the present disclosure enable one or more of the following unique features or advantages: a close-packed array of linear microchannels (e.g., each microchannel having an inner diameter of ≥10 μm to ≤450 μm) that emulate native nerve organization as shown in FIG. 2A; microchannels having significant and customizable lengths; thin walled microchannels to maximize open volume (e.g., walls having a thickness of 10-30 micrometers); high open lumen volumes (e.g., >90% in certain variations); tissue scaffold devices comprising biocompatible materials, like FDA-approved polymer materials (e.g., PCL and PLGA); an ability to control mechanical properties to optimize for strength to minimize wall thickness and suture-ability as an outer sheath tube; an ability to control scaffold and sheath porosity to prevent axon penetration while allowing permeation of oxygen and other nutrients; an ability to modify microchannel surface properties to enable cell attachment; a single one-piece sheath and scaffold construction facilitating ease of implantation enabling secure apposition between nerve stumps and scaffold walls; and finally low material and fabrication cost. FIGS. 2B-2C show cross-sectional schematics of two different high lumen volume nerve repair scaffolds which ideally match or emulate a nerve's native architecture according to certain aspects of the present disclosure. The design in FIG. 2C has a higher microchannel density than a microchannel density in FIG. 2B.

In accordance with other aspects of the present disclosure, a new material processing technology is provided to enable the manufacturing of microchannel nerve guidance scaffolds with high lumen volume comprising biocompatible polymer materials.

As noted above, many conventional nerve tissue scaffold devices are formed from hydrogels, which are too weak to form thin-walled microchannels. In replacing hydrogels, several FDA approved synthetic polymers exhibit greater than 100 times in strength compared to hydrogels. However, these polymers also exhibit stiffnesses (elastic modulus) that are significantly (approximately >100 MPa) higher than host nerve tissue (that is about 8 kPa), which could compromise biocompatibility. Generally, it is believed that the nerve guidance scaffold material should be comparable to that of the host nerve tissue to minimize inflammation. Thus, in one aspect, the present technology provides an approach to reduce the stiffness of synthetic polymers to improve biocompatibility of the tissue scaffold devices. However, it has been surprisingly found that the tissue scaffolds of the present disclosure may have a relatively high modulus, but inflammatory response when implanted remains desirably low showing good biocompatibility.

Additionally, it is believed that nerve regeneration scaffold walls may require interconnected porosity to allow nutrients and oxygen to permeate laterally between microchannels and the scaffold periphery. Introducing porosity can also lower the elastic moduli. Conventionally, templating by using a porogen, in particle form, may be used to displace volume in a polymer as it polymerizes/solidifies. Once polymerization is complete, the porogen/polymer construct is immersed in a solvent to selectively dissolve the porogen to create pores. However, conventional porogen particles, such as sodium chloride (NaCl) particles have relatively large particles sizes that produce pore diameters of greater than about 63 micrometers. Thus, use of such a conventional porogen size would not permit formation of thin scaffold walls (e.g. having a thickness<50 microns) and would undesirably create line-of-sight voids that axons could penetrate. Additionally, these relatively large pores/discontinuities would compromise the scaffold mechanical integrity.

In accordance with certain aspects of the present disclosure, a porogen is prepared by reducing particle size and then used to template FDA-approved synthetic polymers for nerve repair. By reducing the porogen dimensions (e.g., to less than or equal to about 10 micrometers in certain variations), synthetic polymer scaffold walls comprising numerous interconnected, pores having a reduced average pore size (e.g., less than or equal to about 10 micrometers) are created. The reduction in pore size thus serves to desirably eliminate line-of-sight pores that could allow axons to grow between microchannels, while maintaining adequate mechanical strength of walls formed from the porous polymers.

The present disclosure provides in certain variations methods of making a tissue scaffold for neural tissue growth. The method may comprise admixing one or more porogens and a polymeric precursor solution together. The ratio of the polymer to porogen determines the volume % of the polymer and can be selected based on the targeted porosity and mechanical properties. The polymeric precursor solution may include a polymeric precursor and a first solvent.

The porogen may have an average particle diameter or size of less than or equal to about 40 μm, optionally less than or equal to about 30 μm, optionally less than or equal to about 20 μm, and in certain variations, optionally less than or equal to about 10 μm. The porogen is preferably a material that is brittle and soluble in a second solvent that does not dissolve in the first solvent/polymeric precursor solution. As a rough estimate, a ratio of bulk modulus to the shear modulus indicates the ductile/brittle behavior of a solid. According to Pugh's criterion, a critical value for a transition from brittle to ductile behavior is 1.75. Thus, to facilitate particle reduction via mechanical comminution, porogens may be selected as having Pugh ratios of less than 1.75. In certain variations, the porogen is selected from a group consisting of: sodium chloride, calcium chloride, potassium chloride, sugars, and combinations thereof. A sugar may be selected from the group consisting of: sucrose, maltose, lactose, fructose, glucose, galactose, and combinations thereof.

NaCl is a particularly suitable porogen owing to its insolubility in solvents used to dissolve biocompatible polymers (such as polycaprolactone (PCL) and polylactic co-glycolic acid (PLGA)) and its solubility in water, which does not readily dissolve PCL or PLGA.

To reduce the porogen size, a mechanical comminution technique may be used to mill or pulverize porogen particles (such as NaCl). In certain variations, the method may thus comprise reducing a particle size of a precursor of the porogen by ball milling the precursor before admixing it with the polymeric solution. In other variations, a planetary ball mill may be used to mill the porogen to reduce powder particle size. The mixing may be for greater than or equal to about 1 minute to less than or equal to several hours, for example, less than or equal to about 2 hours, optionally less than or equal to about 1 hour. The speed of the mixing may be conducted at 100 RPM to 400 RPM. In certain aspects, the mixing may be conducted at 400 RPM for 30 minutes.

In FIG. 3, Step 1a shows reducing the porogen particle size by using planetary ball milling. Planetary ball milling refers to a type of ball milling process that employs a planetary rotation motion. Planetary ball milling imparts significantly more kinetic energy to powder particles, as compared to conventional ball milling, thus it can achieve smaller particles. However, other forms of milling may be used to reduce particle size of the porogen, where appropriate. A Retsch PM 100 planetary ball mill may be used with a 250 ml agate vial containing twelve 9.1 mm diameter agate mill balls (Hann, Germany). In one variation to obtain the desired average particle size (about 6 micrometers), different ball milling conditions are tested: various vial rotational speeds ranging from 100 to 400 RPM and various milling times ranging from 1 to 60 minutes. Additionally, various combinations of rest times between rotation directions (CW and CCW) are explored. The effect of rest time is studied, because it is known that resting allows the vial contents to cool for improved particle size reduction. In certain variations, suitable although non-limiting ball milling conditions may be 400 RPM for 30 minutes with no rest intervals and only CW rotation.

A reduced particle size porogen may thus be combined with the polymeric precursor solution. The polymeric precursor solution may comprise precursors (such as monomers, comonomers, or oligomers) of any of the biodegradable polymers discussed above, including polycaprolactone, poly(lactic-co-glycolic acid) polymer, or combinations thereof. The solution may further include a first solvent in which the polymer precursor is soluble, such as chloroform, by way of non-limiting example. In certain variations, the polymeric precursor solution may comprise greater than or equal to 0.2% to less than or equal to about 20% by mass or weight of the polymer precursor in the total solution including the first solvent. In certain aspects, the polymeric precursor solution may comprise greater than or equal to about 0.5 weight % to less than or equal to about 5 weight % of polycaprolactone in the first solvent. In other variations the polymeric precursor solution may comprise greater than or equal to about 1 weight % to less than or equal to about 15 weight % of poly(lactic-co-glycolic acid) polymer in the first solvent.

As shown in Step 1b, the polymeric precursor solution may be introduced into the ball-milled porogen. Further mixing of the porogen with the polymeric precursor solution may form a suspension. The mixing may be for greater than or equal to about 1 minute to less than or equal to several hours, for example, less than or equal to about 2 hours or optionally less than or equal to about 1 hour. The speed of the mixing may be conducted at 100 RPM to 400 RPM. In certain aspects, the mixing may be conducted at 400 RPM for 30 minutes. In certain variations, the suspension may comprise a porogen, such as sodium chloride, at greater than 0 volume % to less than or equal to about 80 volume % and either (i) greater than 0 volume % to less than or equal to about 80 volume % of polycaprolactone in the suspension; or (ii) greater than or equal to about 0 volume % to less than or equal to about 95 volume % of poly(lactic-co-glycolic acid) polymer in the suspension.

Step 2 of FIG. 3 includes Steps 2a-2d where a tube is formed. In Step 2a, a template is contacted with the suspension to coat at least one surface with the suspension. The template may have a rod or a fiber shape selected to have a predetermined diameter corresponding to the desired diameter of the coating and ultimately the microchannel formed thereon. The template may be solid or have a hollow core or internal lumen. The template may comprise a metal selected from a group consisting of: brass alloy, copper, stainless steel, and combinations thereof. It should be noted that certain template materials did not appear to work with certain material suspensions in not providing adequate stability or uniform wetting, for example, templates made of graphite, tungsten, and cross-linked polystyrene. Suitable metal materials for the template desirably fulfill the following criteria: (1) wettability by the suspension/slurry to produce a uniform thickness, (2) adequate stiffness to maintain linearity in high aspect ratio form and (3) delamination of the polymer after polymerization.

The template may have a diameter corresponding to the desired diameter of the microchannel to be formed (for example, for a solid template, the outer diameter of the template corresponds to the inner diameter of the microchannel). Thus, any of the diameters discussed above in the context of the microchannel may be appropriate diameters for the template. The template may be significantly longer than the desired length of the microchannel and may be used to form multiple microchannels. The contacting may include immersing the template in the suspension comprising porogen and polymeric precursor to coat the surface with the suspension.

As background on template material selection, while polymer optical fiber templates can be used to fabricate greater than 60 volume % conventional nerve repair scaffolds, they are formed of hydrogels. The solvents used in the precursor solution (e.g., for PCL and PLGA) would readily dissolve the polymer fibers if they are used as templates. For example, optical fiber templating typically are formed of non cross-linked thermoplastic polymers such as polystyrene or polymethylmethacrylate (Paradigm Optics. Vancouver, WA). Because the solvents used to synthesize PCL and PLGA are aggressive (chloroform), the polymer optical fiber templates would readily dissolve. Another template could be a sugar fiber comprising sucrose to create linear channels in PLGA. Sugar is not soluble in the solvents that dissolve PLGA (or PCL). However, the close packing of sugar fibers has not been demonstrated, thus, sugar fibers are unlikely to be able to form a >90% channel lumen volume. Furthermore, sugar is inherently brittle, thus processing high aspect ratio (about 200 micron diameter-1 cm long) fibers would likely be difficult to achieve.

As noted above, instead of using a solvent to remove fiber templates, a metal fiber or rod template is instead used. The template is combined with mechanical/chemical removal that makes high aspect ratio microchannels. In certain aspects, the suspension has adequate viscosity to allow the uniform coating of the template rods while maintaining the uniform dispersion of the porogen. The viscosity of the solution is determined by the concentration of the polymeric precursor solution (e.g., monomer solution), the solvents used, and the volume fraction and size of the porogen included. The viscosity can be optimized by varying one or all of these parameters.

After the template is removed from contact with the suspension, a portion of the first solvent may be removed from the coating formed on the surface of the template as shown in Step 2b. In this manner, the precursor may be polymerized while having the porogen distributed therein to form a coating. In certain aspects, the porogen may be homogenously distributed through the polymer in the coating. Notably, the coating may be formed on the outside of a solid template or on the inside and/or outside of a hollow template. The template may be rotated or moved to facilitate volatilizing the first solvent from the coating. After a portion of the first solvent is removed, the coating that remains on the template surface includes porogen and the polymer.

In certain aspects, the method may further comprise exposing the coating to a lubricant or a delamination agent as shown in Step 2c. The lubricant/delamination agent may be a liquid that aids in delamination and removal of the coating from the surface of the template. The template may be immersed in such a lubricant solution. A suitable lubricant includes methanol. Methanol does not dissolve the template, porogen, or polymer, but does cause the polymer to swell to ease and facilitate delamination.

Next, the coating, comprising the porogen and the polymer, is removed from the template as shown in Step 2d as a tube. The coating may be slid off the template.

After removal, in Step 2e the tube/coating may be cut on one or more ends to form a microchannel. The cutting may be accomplished by mechanical cutting (e.g., by a razor or wire cutter), laser cutting, and the like.

This process may be repeated to form a plurality of microchannels (or a plurality of microchannels may be made in a single process step and cut into discrete microchannels). The microchannel is thus disposed within and assembled inside a sheath with a plurality of other microchannels to form the tissue scaffold, as shown in FIG. 3, Step 3a. The microchannel may be introduced into the sheath or the plurality of microchannels may be assembled and then the sheath formed over the assembled microchannels. The microchannel tubes may be stacked inside the sheath and then can be fused together. Thus, a process to assemble individual microchannels into close-packed arrays is contemplated. The use of such a tube fabrication process can also fabricate relatively large outer sheaths to contain and mechanically support the microchannel array. Additionally, such an outer sheath also assists in the suturing of the nerve stump to the scaffold.

Next, in Step 3b, the microchannels and sheath (comprising the porogen and polymer) are exposed to a second solvent to remove the porogen from the materials. The second solvent dissolves the porogen, but not the polymer. A suitable second solvent may be water. The construct may be immersed in the second solvent, such as water, at ambient temperature and pressure conditions. Excessive heating of the water bath may cause damage to the polymer and thus is desirably avoided. The duration of exposure to the second solvent is sufficient to remove substantially all of the porogen to form a porous material. In certain aspects, exposure to the water may be greater than or equal to about 1 hour up to about 2 days, optionally greater than or equal to about 2 hours up to about 1 day, and in certain aspects, greater than or equal to about 3 hours up to about 18 hours. After removal of the porogen the tissue scaffold is formed that comprises a porous microchannel and/or porous sheath.

An additional step may be conducted that includes coating the tissue scaffold construct with a biofunctional material, as discussed above. In this manner, the scaffold can be coated with a desired protein or molecule to improve biocompatibility and/or cell attachment.

The tissue scaffold may also be sterilized for implantation. For example, the scaffold may be immersed in ethanol for sterilization. In other variations, the sterilization may be exposure to UV radiation or other known techniques that do not degrade or harm the polymeric materials forming the scaffold.

To fabricate microchannel tubes in accordance with certain aspects of the present disclosure, a precursor of a polymer of interest is dissolved in a first solvent and ball milled with the pre-ball-milled porogen. A metal rod is then used as a template and can be coated with the mixture. A polymeric tube is formed around the rod. The diameter of the rod determines the diameter of the tubes. The thickness of the tube formed on the surface of the template rod is manipulated by changing the viscosity of the polymeric solution and the number of coatings. The rod is then removed from the suspension of porogen and polymeric precursor and a hollow polymeric tube is formed. An outer sheath with a larger diameter, equivalent to the diameter of the implant, is fabricated using the same technique. The outer sheath can have a different material composition than the inner microchannel tubes. The inner microchannels and outer sheath are cut to a predetermined length depending upon the end use. The outer sheath can be larger (e.g., longer) than the inner tubes if needed; for example, to provide extra support for the scaffold and/or to have extra space to suture/staple the implant to the tissue. Microchannel tubes are then stacked inside an outer tube and can be fused together. The scaffold is placed inside a solvent that etches away the porogen, but not the polymer. The scaffold may then be sterilized, for example, by using ultraviolet radiation or alcohol treatment.

Various embodiments of the inventive technology can be further understood by the specific examples contained herein. Specific Examples are provided for illustrative purposes of how to make and use the compositions, devices, and methods according to the present teachings.

Example 1

Planetary ball milled porogen NaCl (6 micron diameter average particle size) (Columbus Chemical Industries, INC. Columbus, WI)) is mixed with various concentrations of synthetic polymer, in chloroform (Alfa Aesar. Ward Hill, MA) (FIG. 3, step 1b). PCL (Mn 80,000) (Sigma. St. Louis, MO) and PLGA (85/15) (PCAS. Longjumeau, France) are the polymers investigated in this example, thus various monomer concentrations are investigated and range between 0-10% by weight polymer dissolved in solvent (chloroform). Although a broad range of polymer concentrations can be used, in this example, typically 3.0 wt. % PCL and 6.7 wt. % PLGA are used.

To control the volume % porosity, various volume concentrations of NaCl are added to the monomer solutions ranging between 0% to 90%. To ensure the slurries are well mixed and that the NaCl particles are homogenously wetted by the monomer solution, they are planetary ball milled. For example, the mixture may be ball milled for 20 minutes under the same ball-milling conditions as the NaCl, discussed previously. The slurries are cast into thin-wall tubes according to the process discussed above and shown in FIG. 3.

Such techniques are used to form thin-walled high lumen volume scaffolds for nerve repair. There are several approaches to fabricate open channel nerve growth scaffolds. A variety of metal fibers are used to fabricate channels. A range of metal fibers (a fiber being analogous to rod or wire) are investigated and are selected based on the following criteria: (1) wettability by the slurry to produce uniform thickness, (2) adequate stiffness to maintain linearity in high aspect ratio form and (3) delamination of the polymer after polymerization. Examples of the metal fiber templates investigated are copper (McMaster. Aurora, OH), stainless steel (grade 304) (McMaster), brass (McMaster), tungsten (Goodfellow Corporation. Cambridge, England), and graphite (not a metal, but attempted to be used as a template) (Goodwinds LLC. Mount Vernon, WA). It is also determined that the diameter of the rod affected wetting, which is likely a result of capillary forces associated with the fiber radius of curvatures.

Based on this investigation, the following are selected for the various tube geometries: copper fiber (300 micron outer diameter) is used to make microchannels, stainless steel fiber is used to fabricate 1.6 mm inner diameter (ID) outer sheaths, brass fiber is used to fabricate the 6.8 mm ID outer sheath for pig scaffolds. The general tube fabrication process is described in FIG. 3, Steps 2a-2f, above.

The metal fiber is immersed in the slurry or suspension of porogen and polymeric precursor (FIG. 3 step 2a, for approximately 5 seconds). If necessary, step 2a can be repeated to achieve the desired wall thickness. The wetted metal fiber is removed from the slurry and is manually spun clockwise and counter clockwise to uniformly evaporate the solvent (FIG. 3 step 2b, for about 30 seconds). To aid in delamination, the metal fiber/polymer and porogen construct is immersed in methanol (FIG. 3, step 2c). The methanol does not dissolve the metal fiber, porogen salt or polymer, but does cause the polymer to swell to ease delamination. The tube is mechanically separated by pulling the tube off the wire (FIG. 3, step 2d). Lastly, the tube is cut to the desired length with a razor or laser (FIG. 3, step 2e). Finally, the tube may be immersed or soaked in water (for example, at ambient conditions) in FIG. 3, step 2f.

Assembling the channels into scaffolds is described in FIG. 3, step 3a. The microchannels are assembled into close-packed arrays and inserted into the outer sheath. Because the microtubes have the same diameter, for a given scaffold design, they self-assemble into a hexagonal or honeycomb arrangement to maximize the packing density.

After assembly, the construct is immersed in water (24 hours) to selectively remove the NaCl porogen contained in the walls of the tubes (microtubes and outer sheath) as shown in FIG. 3, step 3b.

Subsequent immersion in ethanol sterilizes the scaffold for implantation.

Example 2

Figure 4A:
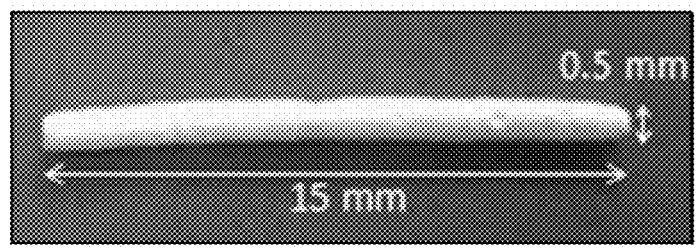
Figure 4B:
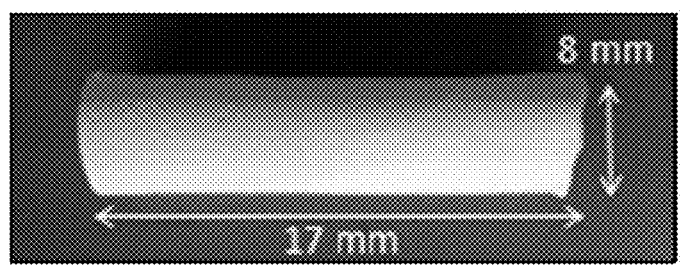
Figure 4C:
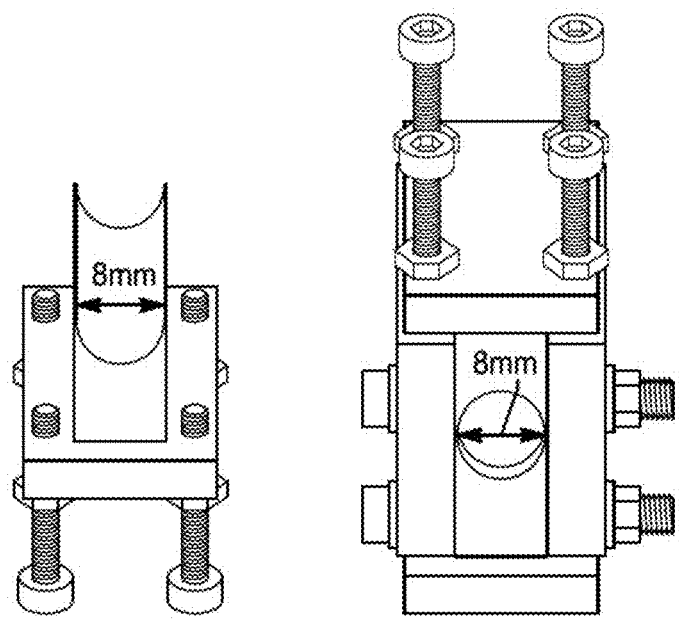
Figure 4D:
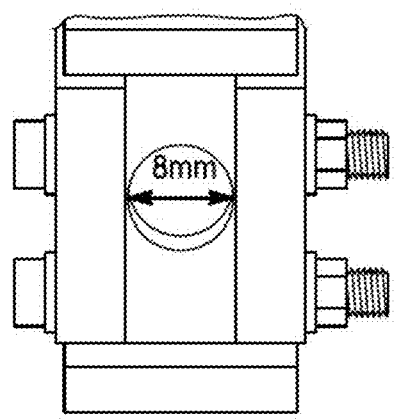
Figure 5A:
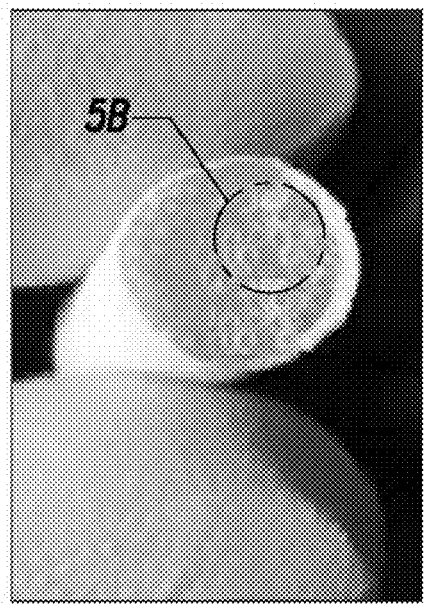
Figure 5B:
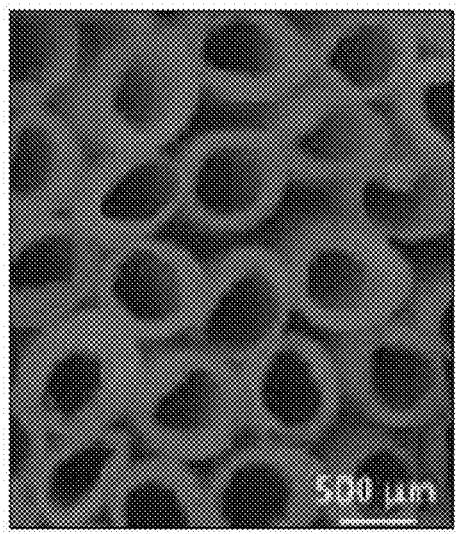
Figure 5C:
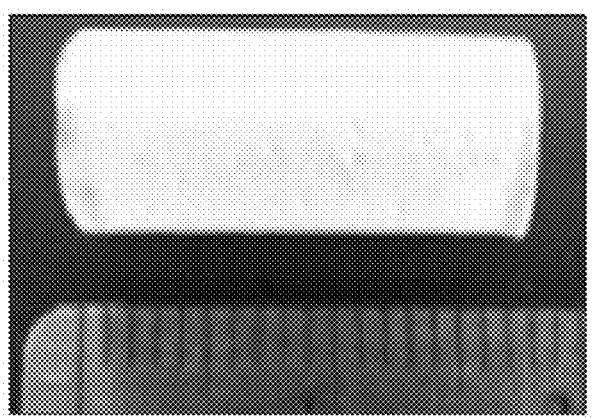

The fabrication of a PCL microchannel scaffold for implantation into a pig sciatic nerve model is shown in FIGS. 4A-4D. As shown in FIG. 4A, the microchannels (15 mm long, 280 microns inner diameter (ID), 30 micron wall thickness) are assembled in a custom fabricated clam shell, slotted die fixture (FIGS. 4C-4D). The microchannels are stacked and compressed to create an ordered array of microchannels. Once stacked, an outer sheath (6.8 mm ID) shown in FIG. 4B is inserted between the microchannel array periphery and inner lining of the clam shell fixture. 60 micro channels are packed into the 6.8 mm ID outer sheath creating a 90% open lumen volume scaffold. A microchannel density of 120 microchannels/mm$^2$ is formed with this scaffold. See FIGS. 5A-5C. This scaffold is implanted in a pig sciatic nerve model for in vivo and functional recovery testing.

Microstructural Analysis

Figure 6:
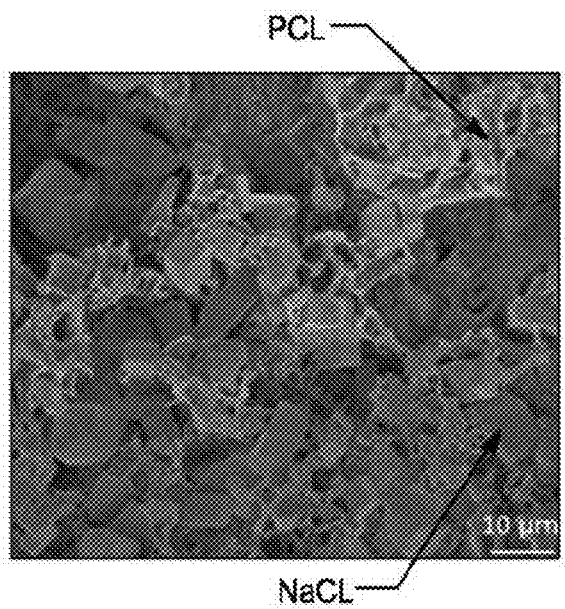

To characterize the effect the porogen had on porosity, scanning electron microscopy (SEM) is conducted. In FIG. 6, the fracture surface of a typical PCL and NaCl construct before salt leaching (immersion in water to selectively remove NaCl) is shown. After planetary ball milling, the average NaCl particle size is 17 microns. FIG. 6 also shows the NaCl dispersed in the PCL.

Figure 7A:
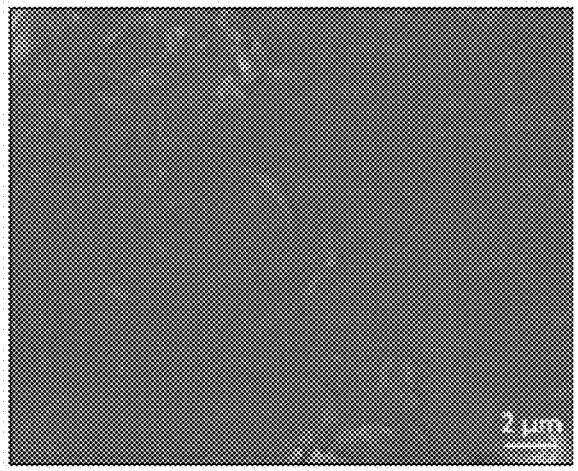
Figure 7B:
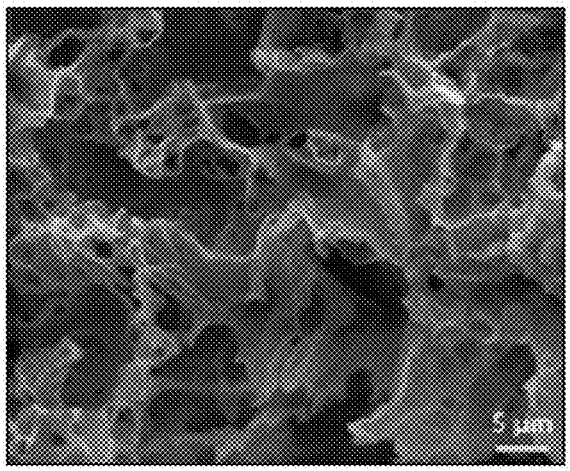

FIGS. 7A-7B compare pure PCL polymer (no NaCl porogen in FIG. 7A) as compared to salt-templated PCL in FIG. 7B. FIG. 7B shows how the NaCl porogen creates porosity. Although not described in detail, there is evidence to suggest that when the NaCl is below a certain diameter (believed to be somewhere between about 17 and about 50 microns) and a relatively high volume fraction of NaCl (approximately >50%), the porogen disrupts PCL polymerization to create unique porosity unobtainable with the previous state-of-the-art salt leaching processes.

Figure 8A:
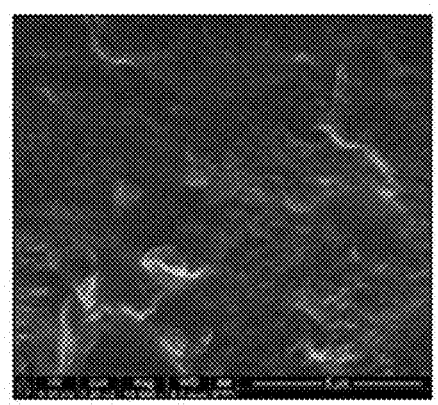
Figure 8B:
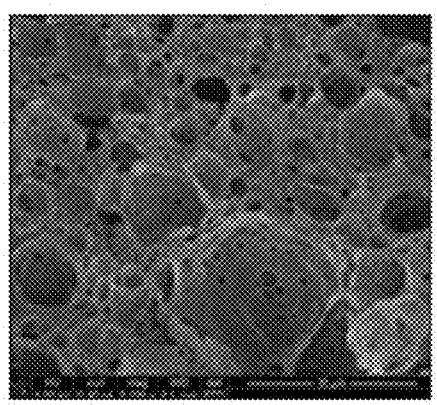
Figure 8C:
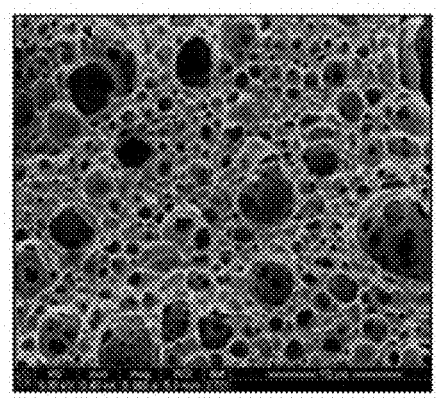
Figure 8D:
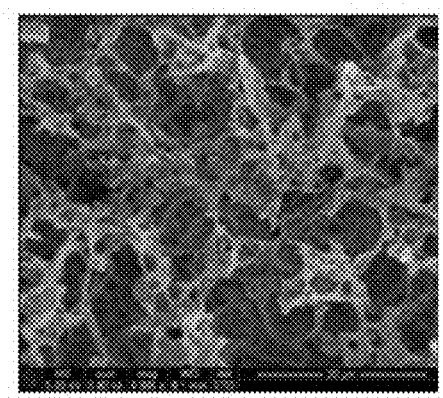

Such a salt leaching process can also be used with other FDA approved biocompatible polymers, such as polylactic co-glycolic acid (PLGA). Porous PLGA is thus formed. Essentially, the process described above in the context of FIG. 3 is used, except an 85/15 (lactic acid/glycolic acid wt. % ratio) replaced the PCL. As shown in FIGS. 8A-8D, the same scale and volume fraction porosity is achieved in PLGA. FIG. 8A shows 0% porosity, FIG. 8B shows 40% porosity, FIG. 8C shows 50% porosity, and FIG. 8D shows 60% porosity. In the context of nerve repair, if the PCL degradation rate is too slow for certain applications, PLGA is a viable alternative owing to its faster degradation rate.

Figure 9:
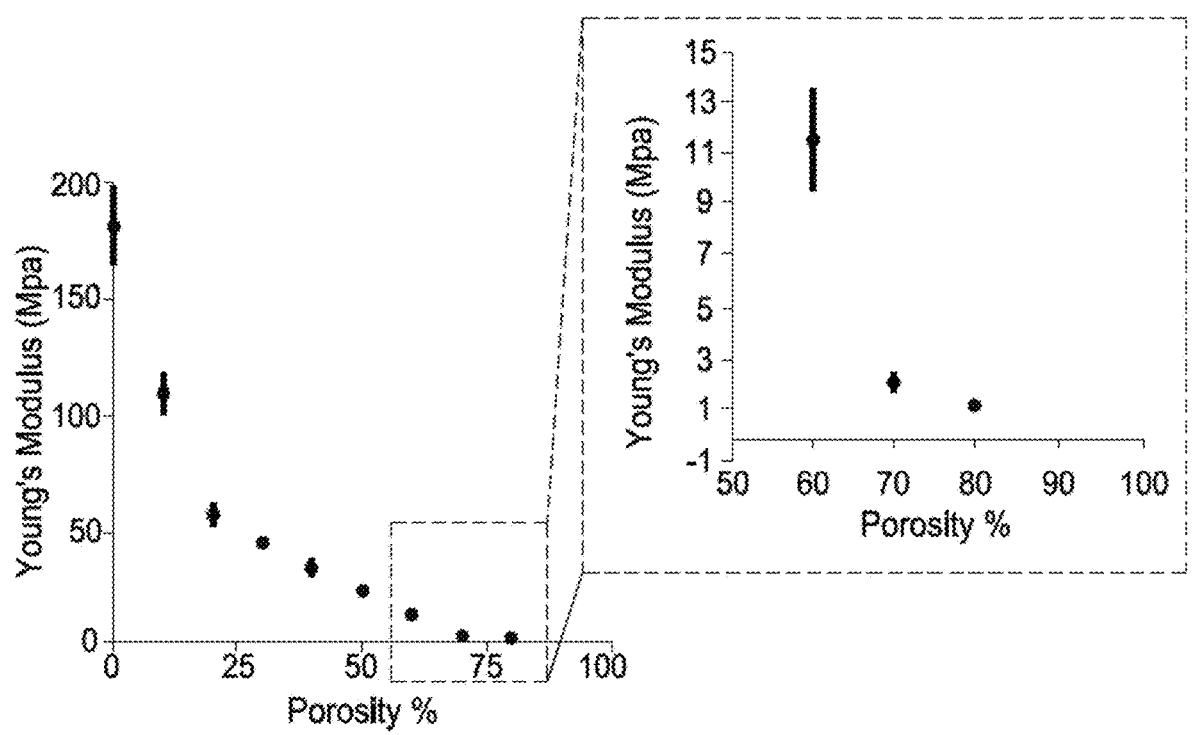

By controlling the volume fraction of porosity, the following aspects can be tuned: elastic modulus, strain to failure, strength, degradation rate, and cross-flow of nutrients between microchannels. Preliminary data demonstrate the correlation between the volume fraction of porosity (or PCL volume fraction which is equal to 1 vol. % porosity) and the elastic modulus (stiffness) in NaCl-templated PCL (FIG. 9). From FIG. 9, it can be seen that the elastic modulus is sensitive to the volume fraction porosity over a broad range. For example, the elastic moduli for the 20 and 100 vol. % PCL are 1.1 MPa and 182.1 MPa, respectively. The elastic modulus value of 1.1 MPa is within a factor of four compared to the 3 wt. % agarose (0.3 MPa) that has been used previously and is compatible with nerve tissue. Additionally, the value of 182.1 MPa for 100% PCL is in agreement with literature values for pure PCL.

The scaffolds have been designed, fabricated, and implanted in vivo in rodents, and pigs. Compared to state-of-the-art (SOA) single-lumen devices (such as commercially available INTEGRA® and NEUROLAC® scaffold devices), the sheath and scaffold technology according to the present teachings enable linear axon guidance and distal axonal penetration into host tissue. Below are three examples of scaffolds designed and fabricated with in vivo efficacy testing: (1) a salt-templated PCL sheath combined with a previous generation hydrogel microchannel scaffold in the PNS; (2) a salt-templated PCL sheath and a microchannel scaffold prepared according to certain aspects of the present disclosure in the PNS; and (3) a salt-templated sheath and a microchannel scaffold prepared according to certain aspects of the present disclosure implanted in the CNS.

Figure 10A:
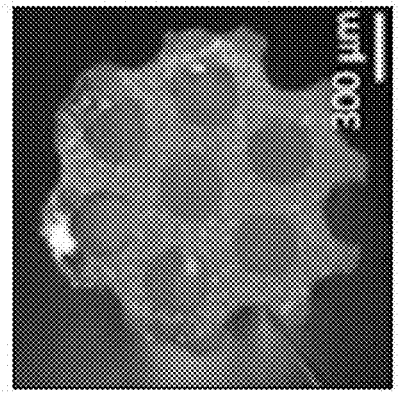
Figure 10B:
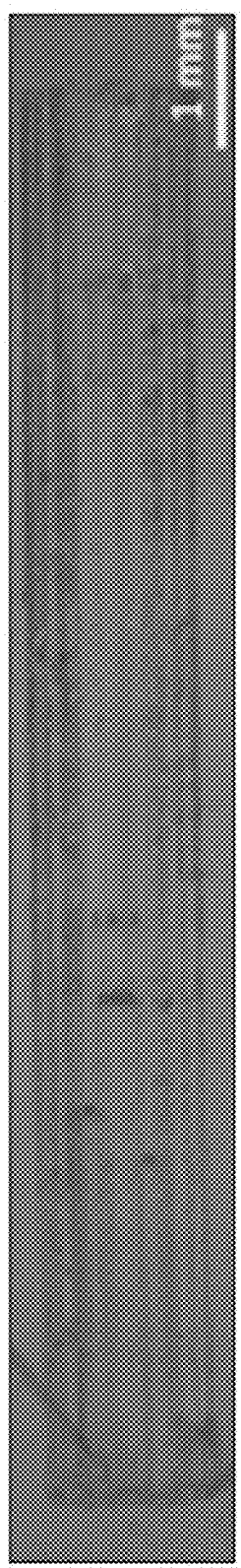
Figure 10C:
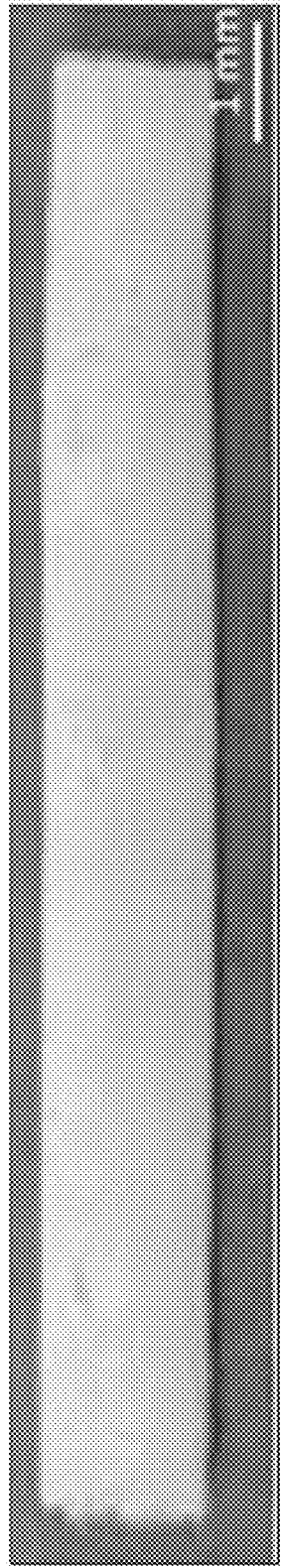
Figure 11:
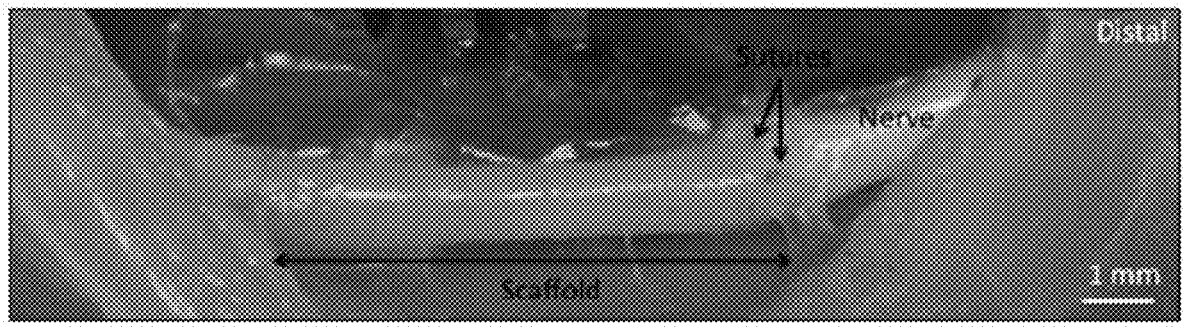
Figure 12A:
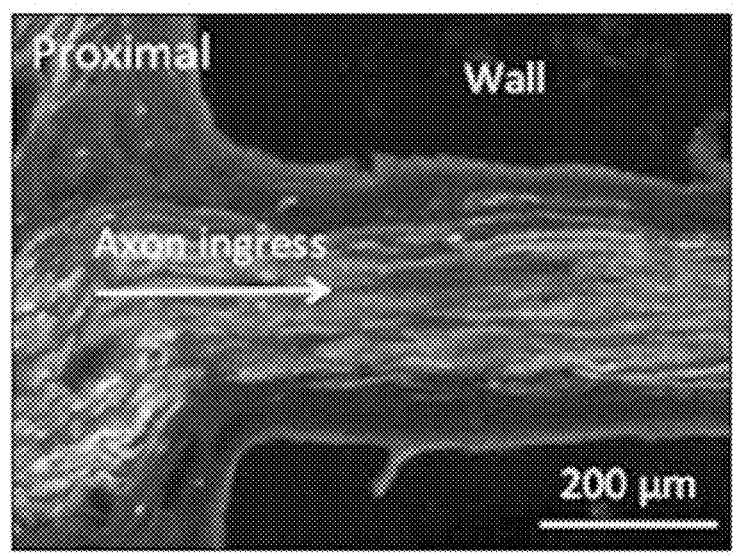
Figure 12B:
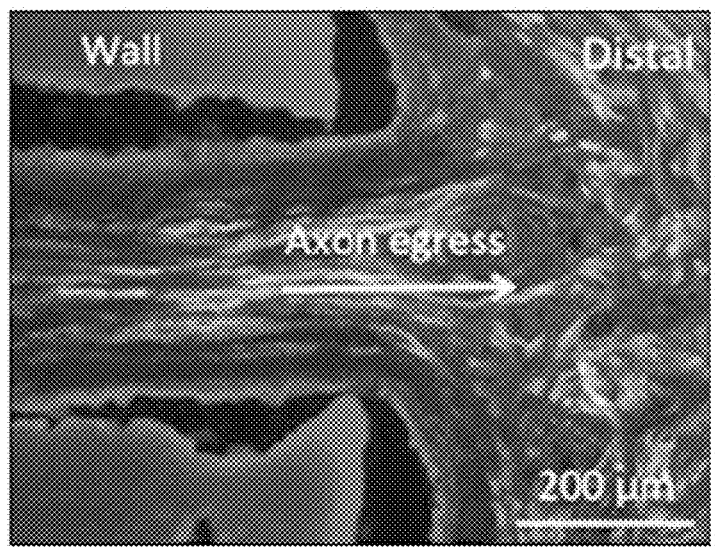

In Vivo Efficacy Testing for Salt-Templated PCL Sheath with Agarose Microchannels To demonstrate the utility of salt-templated PCL sheaths in the PNS, 1.1 mm ID, 1.1 cm long 30 vol. % PCL sheaths are fabricated (70 vol. % porosity) according to certain aspects of the present disclosure as shown in FIG. 10C. 1 cm long agarose microchannel scaffolds are micro-drilled consisting of linear, 300-micron inner diameter channels (FIGS. 10A-10B). The agarose scaffolds are inserted into PCL sheaths and implanted into Fischer rat sciatic nerves by an orthopedic surgeon. The PCL sheaths are sutured to the sciatic nerve stumps on the proximal and distal ends. After eight weeks in vivo, macroscopic analysis shows the integration of the nerve stumps to the PCL sheaths is maintained, the PCL sheath remained intact, and the sutures are still in place (FIG. 11). Eight weeks post-implantation, histological analysis indicated robust axon ingress and egress is achieved over the 1 cm long microchannels, as shown in images at the proximal and distal ends of the PCL sheath in FIGS. 12A-12B, In addition, robust integration of Schwann cells with regenerated axons is apparent.

Figure 13A:
Figure 13B:
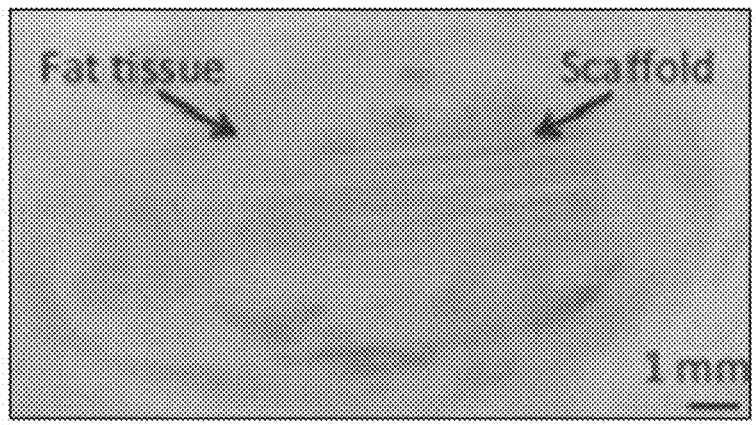
Figure 13C:
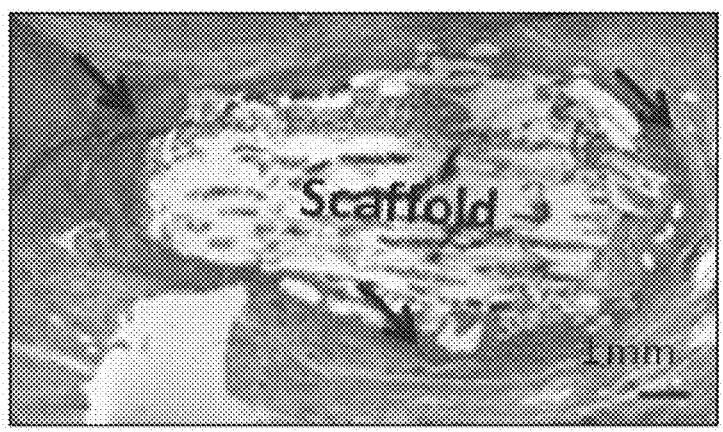

Previously, chitosan-based sheaths in rat and pig sciatic nerve models were studied. In all cases, and despite the use of the low endotoxin grade, significant inflammation occurred. For example, a first generation hybrid chitosan-sheath and agarose micro-channel scaffold was implanted in a pig (FIGS. 13A-13C). The scaffold/lesion cavity was encapsulated in inflammatory tissue due to the presence of the chitosan. Thus, in comparison, the salt-templated PCL sheaths according to certain aspects of the present disclosure appear to be superior to commercial products based on chitosan such as the single-lumen product produced by MEDOVENT® (GmbH).

Salt-Templated PCL Sheath and PCL Microchannel Scaffold in the PNS

To demonstrate the utility of salt-templated PCL sheaths and PCL microchannel scaffolds prepared in accordance with certain aspects of the present teachings in the PNS, 1.1 mm ID, 1.1 cm long PCL sheaths are fabricated (30 vol. % PCL, 70 vol. % porosity). Several 1 cm long, 300-micron inner diameter salt templated microchannel scaffolds are fabricated using the process outlined in FIG. 3 and as discussed previously. The scaffolds are implanted into Sprague-Dawley rat sciatic nerves by an orthopedic surgeon. The PCL sheaths are sutured to the sciatic nerve stumps on the proximal and distal ends. Eight weeks post-implantation, histological analysis indicated robust axon ingress and egress is achieved over the 1 cm long microchannels (FIGS. 14A-14C). In addition, robust integration of Schwann cells with regenerated axons is apparent.

Salt-Templated PCL Sheath and PCL Microchannel Scaffold in the CNS

Figure 15:
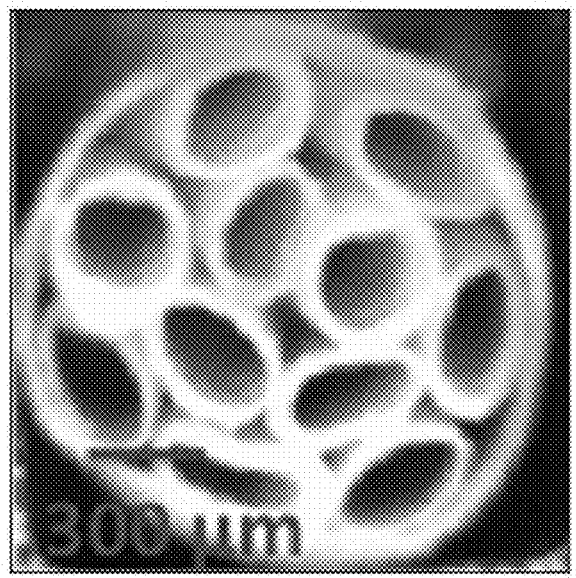
Figure 16:
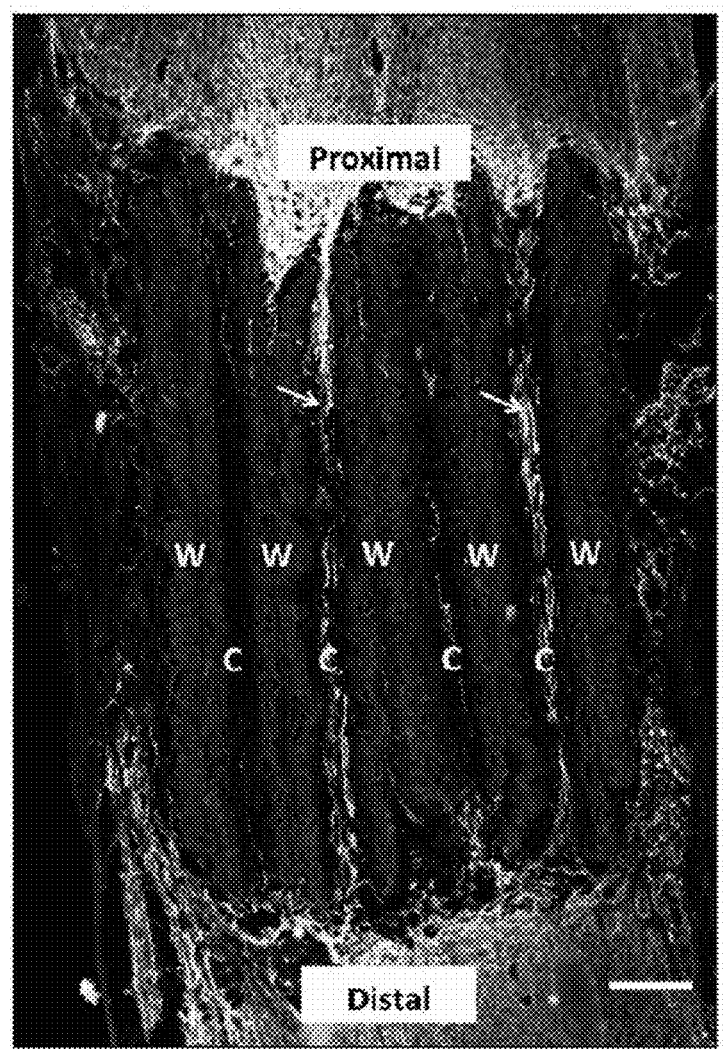

To demonstrate the utility of salt-templated PCL sheaths and PCL microchannel scaffolds prepared according to certain aspects of the present disclosure in the CNS, 1.8 mm ID, 2 mm long PCL sheaths are fabricated (30 vol. % PCL, 70 vol. % porosity). Several 2 mm long, 260-micron inner diameter salt templated tubes are inserted into the 1.8 mm ID tube (FIG. 15). The scaffolds are implanted into Fisher 344 female rat T3 full transection lesion cavities. Four weeks post-implantation, histological analysis indicated the PCL scaffolds remained intact and that, despite the addition of growth factors, there is clear evidence of linear axon guidance and egress (yellow arrows in FIG. 16).

FIGS. 17A-17C show cell attachment on a control and PCL materials for purposes of comparison. 3T3 fibroblast cells are stained for actin and nucleus. FIG. 17A shows a positive control of cell growth in a well plate. FIG. 17B shows cell growth on non-porous PCL (100% by volume PCL). FIG. 17C shows 3T3 fibroblast cell growth on a porous PCL prepared in accordance with certain aspects of the present disclosure having 30 volume % PCL (70 volume % porosity). The cells do not attach to the non-porous PCL film in FIG. 17B, but attach to the porous PCL in FIG. 17C. While not limiting to any particular theory, this may be attributable to the improvement in wettability of the porous PCL material.

FIGS. 18A-18C show that the walls of microchannels formed have interconnected porosity, which is important for transportation of nutrition, waste, and oxygen from cells contained inside the scaffold. FIG. 18A shows an SEM of the surface of the inner wall, FIG. 18B an SEM of the cross-section of the wall, and FIG. 18C the outer surface of the wall of the microchannel.

Figure 19A:
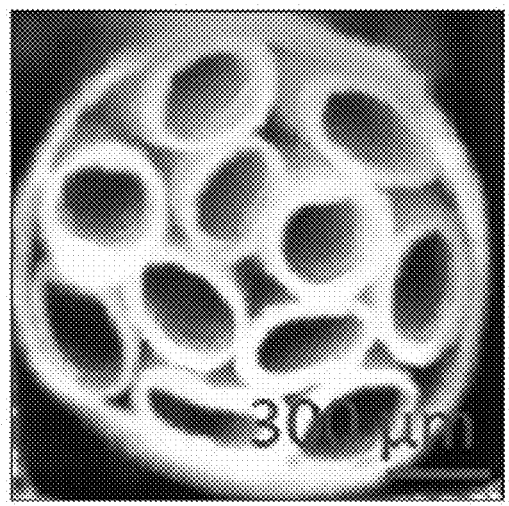
Figure 19B:
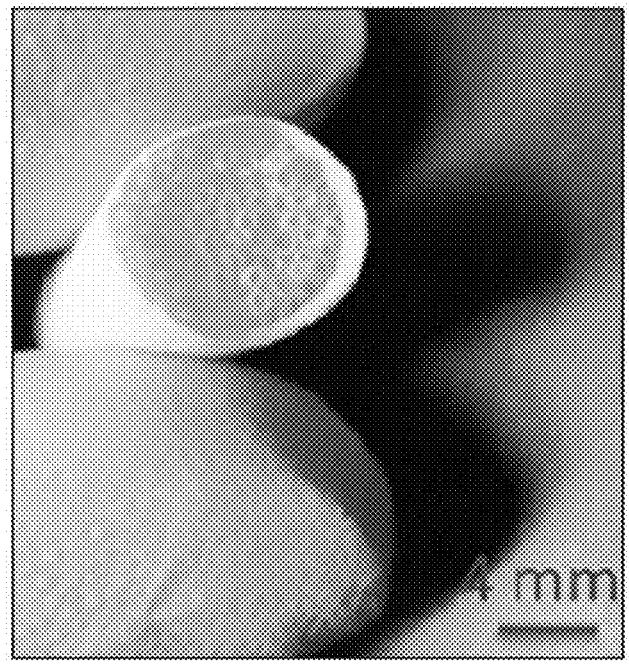

FIGS. 19A and 19B show two PCL tissue scaffolds made in accordance with certain aspects of the present disclosure both having over 85% open volume. FIG. 19A is rat spinal cord tissue scaffold (scale bar is 300 µm), while FIG. 19B is a pig sciatic nerve scaffold (scale bar is 4 mm).

Example 3

Two types of microchannel tubes are prepared; microchannels to guide nerves and large diameter sleeves to serve as the sheath that houses the microchannel scaffolds and enables suturing of nerve stumps to the scaffolds. For a rat model scaffold, a stainless steel rod with a diameter of 1.6 mm is used. Copper wires with diameters of 300 µm are used to fabricate the inner tubes. For a pig PNS scaffold, a stainless steel rod with 6.8 mm diameter and brass wires with a diameter of 500 µm are used to fabricate the outer sleeve and the inner tubes, respectively. The rod or wire is placed in a suspension comprising 70 vol. % of salt porogen and PCL or PLGA in solution. The rod or wire is then quickly removed and spun while holding the rod/wire horizontally to dry off the solvent. For pig scaffold inner tubes and outer sleeves, this process is repeated one more time. The polymer-coated wire/mold is then placed in methanol and the polymeric tube is gently extracted. The tubes are then cut to 1 cm for rat model and 1.5 cm for pig model. Since the tubes generally clamp together after being cut, a copper wire of 200 µm in diameter is passed through the tubes to open them (thus ensuring patency of the inner central lumen).

Figure 20A:
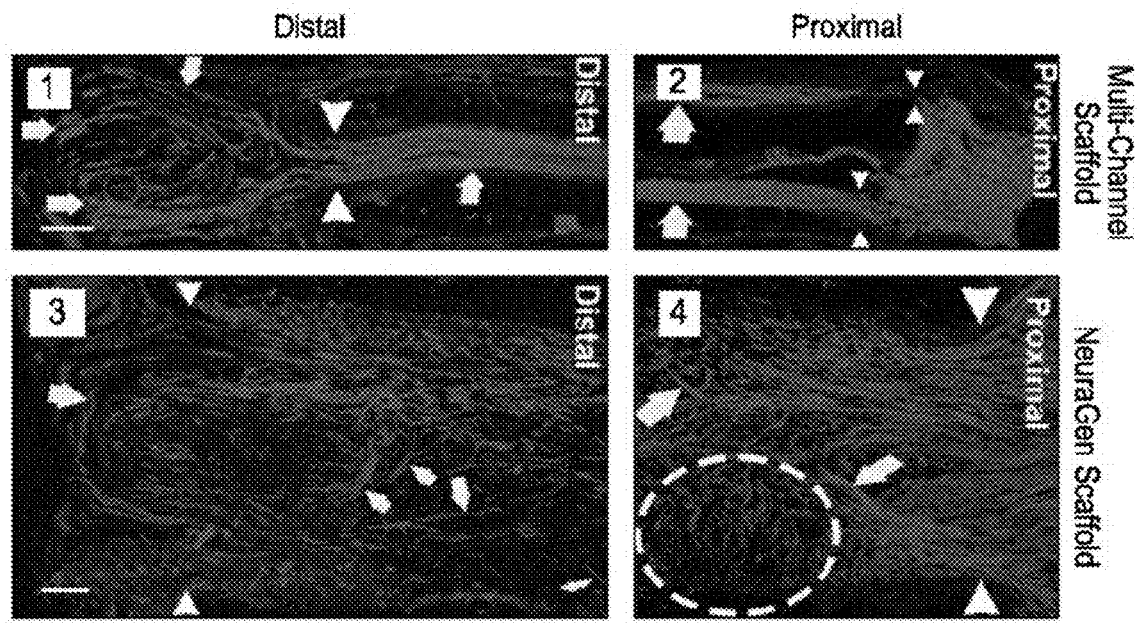

In substantial work done with transected rat sciatic nerve model, scaffolds containing linear guidance channels with diameters of 200 µm have been observed to support highly linear regeneration of injured peripheral axons. FIGS. 20A(1) and 20A(2) show distal and proximal ends of a multichannel 10 mm PCL scaffold prepared in accordance with certain aspects of the present disclosure in transected rat sciatic nerve, 4 weeks post implant. Axons are labeled in red using NEUROFILLAMENT™ 200 stain. Arrow heads point where the proximal transected nerve stump is anastomosed to the scaffold. Full arrows point to linear axons in the channels on the proximal and distal parts of the scaffold as well as in the egress. As shown in FIG. 20A (including FIGS. 20A(1)-20A(4)) a 10 mm polycaprolactone (PCL) implant has many packed linear axons in the proximal as well as the distal part of the scaffold. These axons acquired and kept a linear trajectory as they exit and continue through the distal nerve stump (FIG. 20A(1)).

However, as shown in FIGS. 20A(3)-20A(4), a comparative conventional NEUROGEN™ open tube scaffold (sold by Integra LifeSciences) 4 weeks after implantation in the rat transected sciatic nerve has many axons losing linear orientation even on the proximal side, merely 200 µm after they enter the scaffold. FIG. 20A(4) (full arrows and circle where axons are perpendicular to regeneration axis). The axons are less dense and the few that reach the distal side are not oriented even if they exit to the egress into the distal nerve. FIG. 20A(3). This misguidance of axons can cause pain due to neuroma.

Figure 20B:
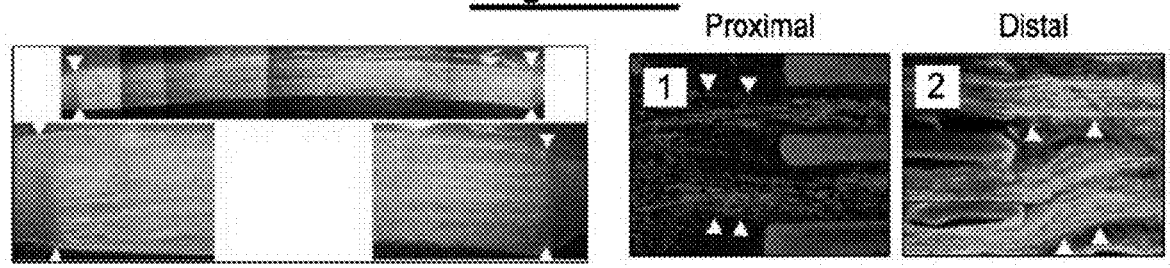
Figure 20C:
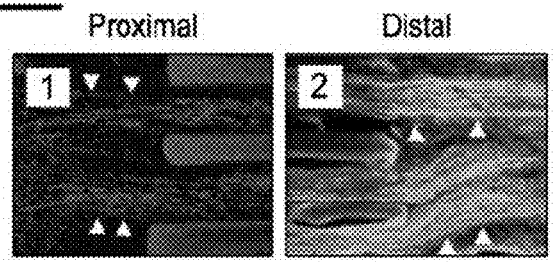
Figure 20D:
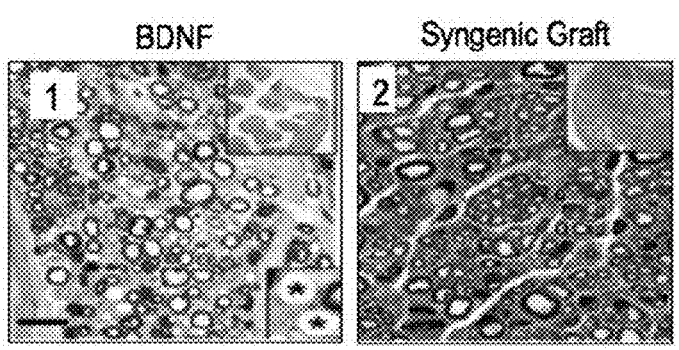
Figure 20E:
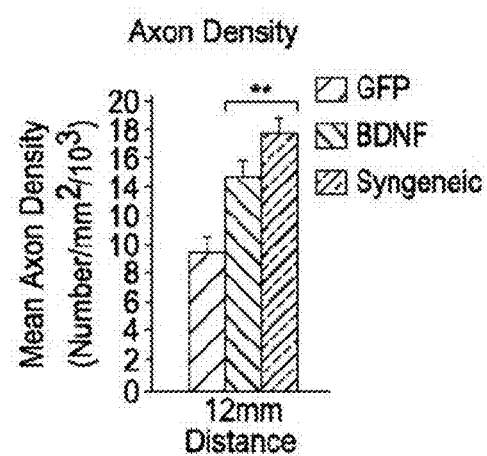

A 15 mm implant prepared in accordance with certain aspects of the present disclosure showed good integration with the nerve stumps as well (FIG. 20B). The scaffold is loaded with BDNF secreting-marrow stromal cells in order to augment the number of axons entering the scaffold. In addition, distal nerve injection of BDNF is performed to attract regenerating axons to exit the scaffold into the distal nerve. The result is extensive emergence of regenerating axons from the scaffold in BDNF treated animals (FIGS. 20C(1) and 20C(2) showing proximal and distal sides. A cross-section of the microchannels shows many myelinated axons in the BDNF treatment, similar to an autograft as well as vascularization (FIGS. 20D(1) and 20D(2) showing the BDNF cross-section and syngeneic graft cross-section, respectively). Quantification of axon density 12 mm within the scaffold indicates that in BDNF group axon density in channel core is similar to syngeneic nerve autografts. FIG. 20E. These successful results in a rat led to the scale up of the scaffold technology in the porcine model.

Figure 21A:
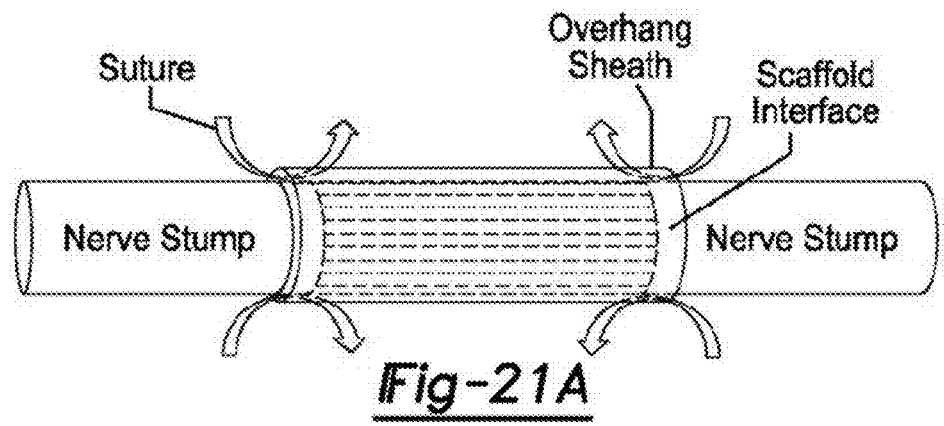
Figure 21B:
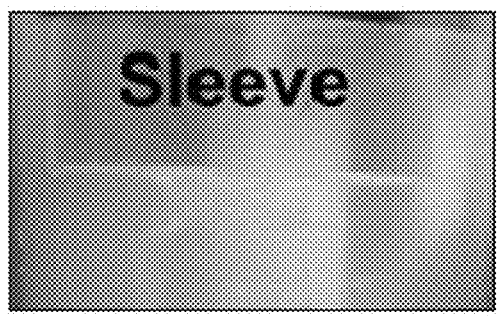
Figure 21C:
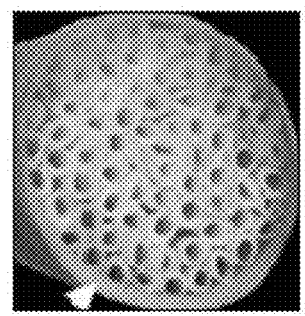
Figure 22A:
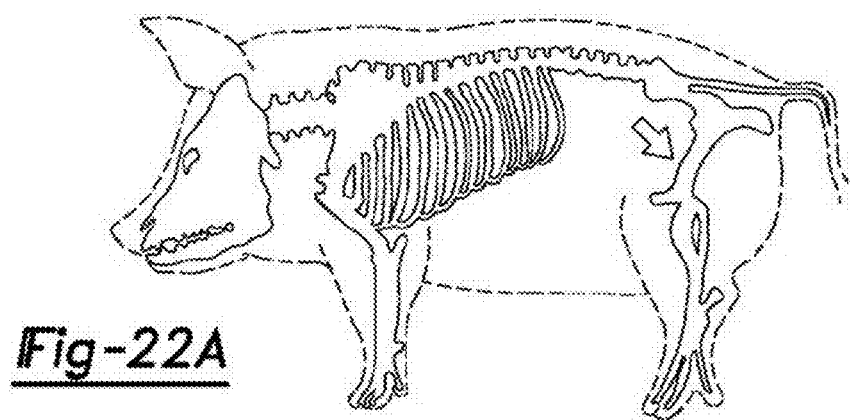
Figure 22B:
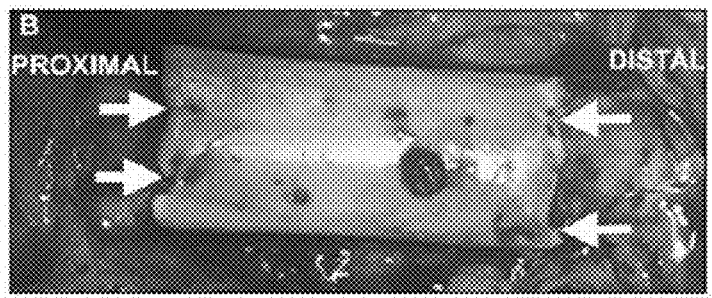

To further improve certain variations of the scaffold implant, a sheath design is used that envelopes the scaffold and extends 1.5 mm over the edges of the scaffold (FIGS. 21A-21C). The scaffold may be anastomosed to the epineurium without suturing directly to the scaffold and thus damaging the structure. It also simplified the implantation procedure for the surgeon, as it is becomes a common anastomosis as being done in human patients with predicated devices that are hollow tubes.

Figure 23A:
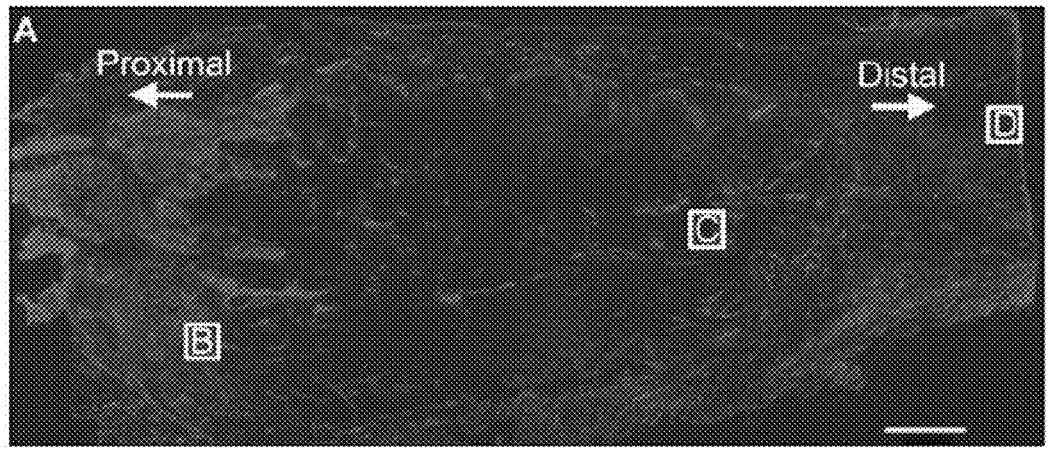
Figure 23B:
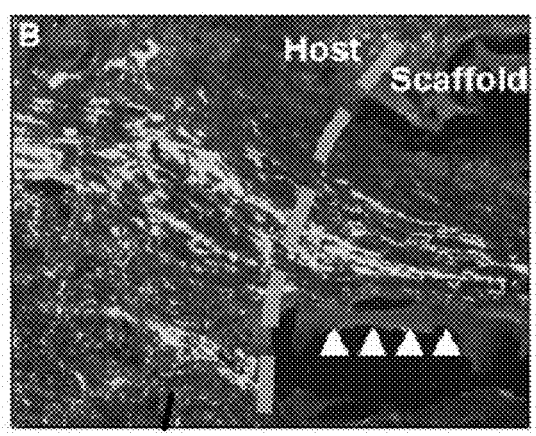
Figure 23C:
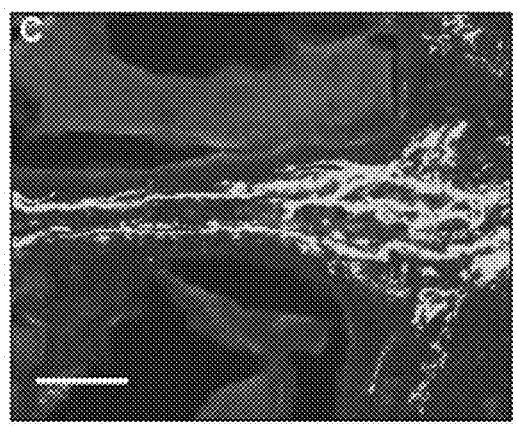
Figure 23D:
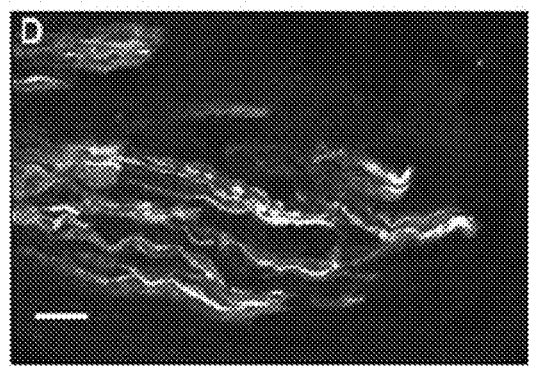
Figure 24A:
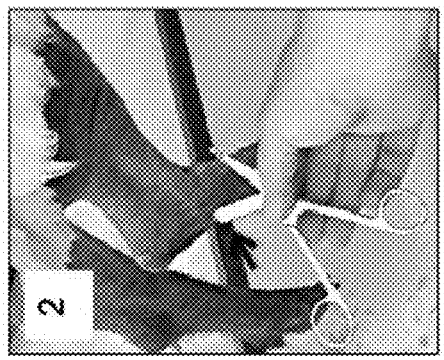
Figure 24B:
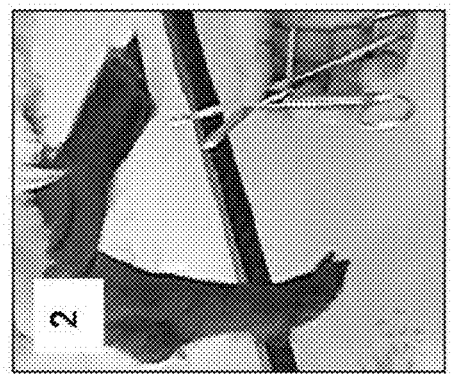
Figure 24C:
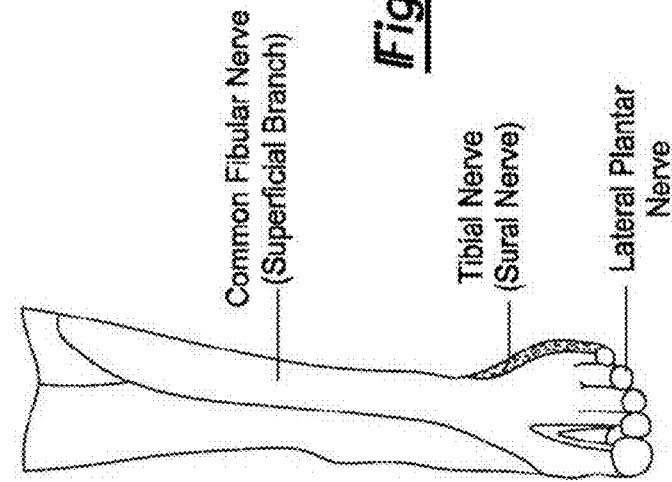

After complete transection of the porcine sciatic nerve 5 cm rostral to the lateral femoral epicondyle, a 15 mm-long PCL scaffold prepared in accordance with certain aspects of the present disclosure is implanted into the injury site. When examined 3 months later, scaffolds are found to have integrated efficiently. The scaffolds support linear axonal regeneration over the gap (FIGS. 22A-22B and FIGS. 23A-23D); axons are observed in the distal stump of the nerve, 3 mm beyond the scaffold (FIG. 23D). Several regenerating axons became remyelinated by Schwann cells (FIG. 23D). Some sensory function is restored to the skin of the lateral front part of the leg (FIGS. 24A-24C). A tester applies pressure to the skin on different parts of the leg (arrows) and looks for limb retraction away from the stimulus. In FIGS. 24A(1)-24A(3) just after transection of the sciatic nerve, the pig's leg did not move. FIGS. 24B(1)-24B(2) show preliminary results 3 months post scaffold implant. The testing detected sensitivity in the lateral front part of the leg (FIG. 24B(1), arrow). There is a prompt withdrawal of the limb as shown in FIG. 24B(2) indicating recovery of sensory function. FIG. 24C shows the area on the skin is innervated by the Common fibular nerve—a branch of the sciatic nerve.

Figure 25A:
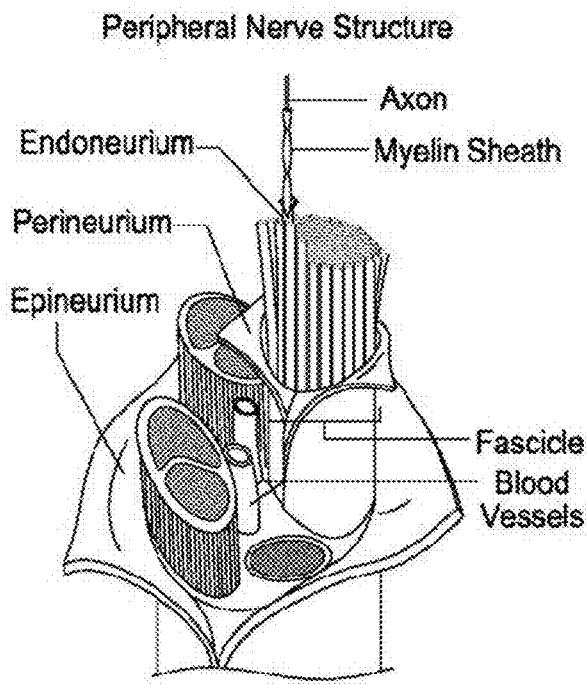
Figure 25B:
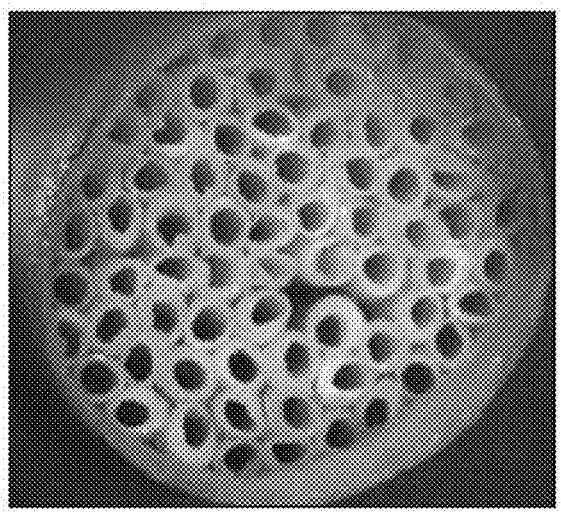
Figure 25C:
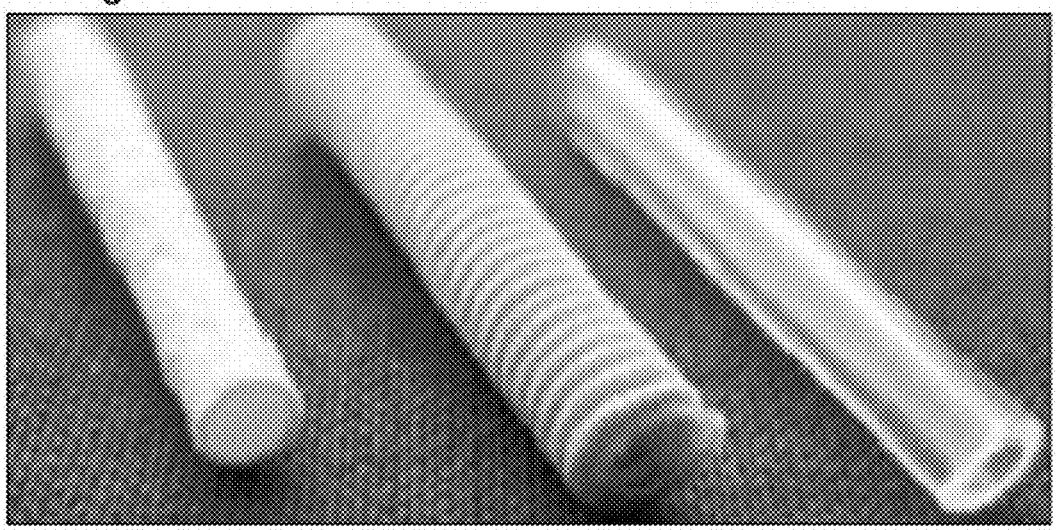

FIG. 25A is a schematic of the anatomical structures present in a representative peripheral nerve structure. FIG. 25B shows a cross-sectional view of a terminal end of a biomimetic micro-scaffold prepared in accordance with certain aspects of the present disclosure designed to mimic the natural architecture of a peripheral neve. FIG. 25C shows comparative commercially available, Federal Drug Administration (FDA)-approved hollow tube scaffold devices from left to right: NEURAGEN™ nerve guide available from Integra Lifesciences Corp., NEUROTUBE™ available from Synovis Microcompanies Alliance, and NEUROLAC™ available from Polyganics. The microchannel scaffold (MCS) device like that shown in FIG. 25B is a technology that facilitates and precisely guides axons across even long peripheral nerve injury gaps. The biomimetic micro-scaffolds prepared in accordance with certain aspects of the present disclosure provide long gap (greater than about 1 cm) peripheral nerve guidance. Guidance is achieved by fabricating devices with precise linear channels to maintain the intact topography of the peripheral nerve with a far greater degree of fidelity than existing, single lumen channels like those shown in FIG. 25C. Thus biomimetic micro-scaffold prepared in accordance with certain aspects of the present disclosure enables a device that micro-aligns specific nerve bundles and guide regenerating axons directly to their respective target from proximal to distal side of the injury mimicking the natural nerve architecture like that shown in FIG. 25A.

Other advantages of the microchannel scaffold technology according to certain aspects of the present disclosure are the unique materials and materials-processing techniques that produce devices that may have: 1) greater than about 60% microchannel open volume or any of the values previously discussed above, 2) high number of microchannels per unit area (for example, about 10-30 microchannels/$mm^2$), 3) microchannel diameters in the range of about 200 micrometers, 4) wall thicknesses of greater than or equal to about 25 to less than or equal to about 67 micrometers, and 5) biodegradable properties. The biomimetic micro-scaffold prepared in accordance with certain aspects of the present disclosures have succeeded in orienting and guiding in vivo axonal regeneration in the spinal cord. No evidence of significant inflammation was observed in in vivo tests. Further, the biomimetic micro-scaffold prepared in accordance with certain aspects of the present disclosure have been used to successfully repair nerve gaps after peripheral nerve injury in rats and pigs.

Example 4

A microchannel scaffold prepared according to certain aspects of the present disclosure formed of polycaprolactone (PCL), containing linear guidance channels about 200 μm in inner diameter, is used with a transected rat sciatic nerve model. The microchannel scaffold device can support highly linear regeneration of injured peripheral axons. FIGS. 26A-26C show comparative growth in transected rat sciatic nerves 4 weeks after implantation. FIG. 26A shows a comparative NEURAGEN™ scaffold, FIG. 26B shows a 10 mm inventive micro-channel scaffold, and FIG. 26C shows an autograft. Green-NF200 stain is used for axons. The interrupted lines demarcate the implant-nerve interface. Excellent integration of the microchannel scaffold device is observed, similar to the predicate device NEURAGEN™ and to an autograft. The arrows on the left point to the proximal side of the implant. A clear reduction in axon density is observed in NEURAGEN™ device (FIG. 26A) while the microchannel scaffold device has similar axon density to the autograft (FIG. 26B). The arrows on the right point to the distal aspect of the implant. Almost no axons reached to the distal part of NEURAGEN™ device, while the inventive microchannel scaffold device kept the same axon density as the autograft (FIG. 26C).

Figure 27:
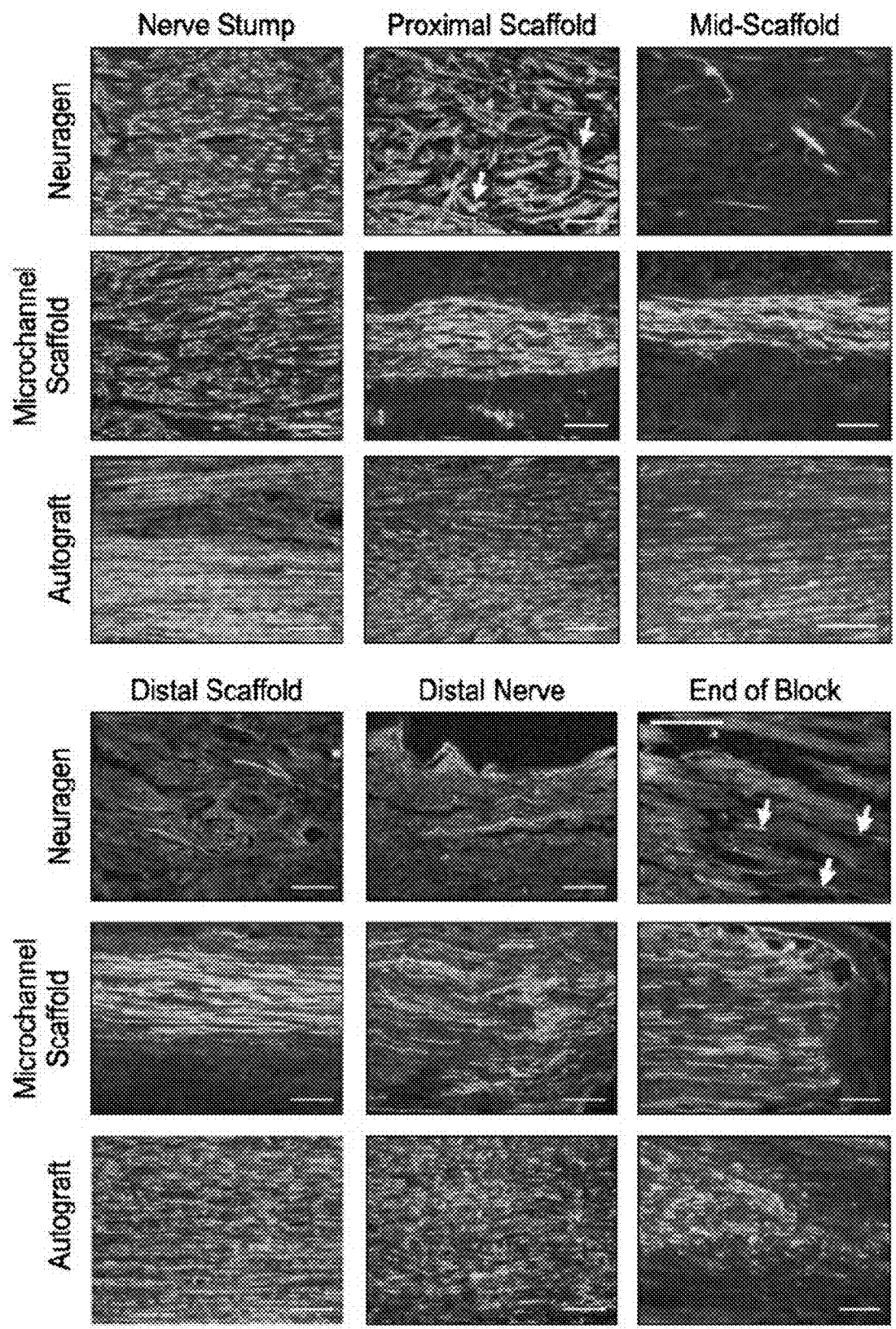

Unlike the comparative scaffold device NEURAGEN™, the inventive microchannel scaffold technology guides axons throughout the gap from proximal to distal while maintaining axonal linearity (FIG. 26B and FIG. 27)). In addition, densely packed and linear axons are detected in the distal nerve and 3 mm beyond the lesion, similarly to the autograft (FIGS. 26A, 26C, and 27). Conversely, the NEURAGEN™ device exhibits a marked reduction in axon density and misalignment within the first few mm of the proximal nerve end, potentially causing neuromas and pain. For example, in the NEURAGEN™ device, axons are already misguided at the proximal side and even turning back (arrows shown in the proximal scaffold). Axons are sparsely positioned on the distal nerve and 3 mm beyond the lesion (arrows in the end of block).

Figure 28:
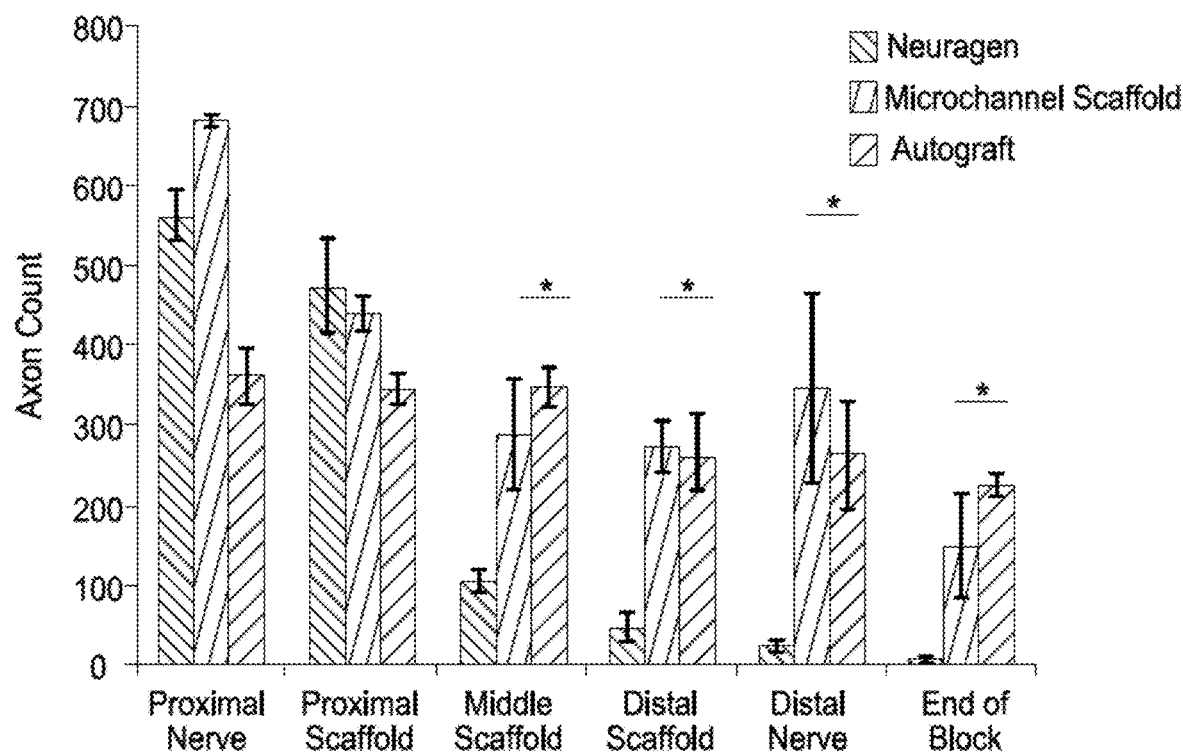
FIG. 28 shows quantification of regenerating axons in different parts of implanted comparative nerve guide devices (NEURAGEN™ nerve guide, a microchannel scaffold device prepared in accordance with certain aspects of the present disclosure, and an autograft) from proximal to distal nerve for a rat transected sciatic nerve, 4 weeks post implantation. ANOVA, mean±S.E.M, $p<0.001$.

Quantifying the axon number in the three groups supports the observation that the number of regenerating axons is reduced dramatically, from proximal to the distal part of the implant in the comparative NEURAGEN™ device. In comparison, the axon guidance and density using the microchannel scaffold technology according to certain aspects of the present disclosure is comparable to that observed in the autograft (FIG. 28). The outer sheath of the inventive microchannel scaffold device also comprises PCL, which is mechanically robust and durable to allow handling and suturing to the nerve stumps. This allowed anastamosis to the epineurium, thus simplifying the surgery as it is becomes a common anastomosis as being done in human patients with commercially available devices that are hollow tube, such as the comparative NEURAGEN™ scaffold.

Figure 29:
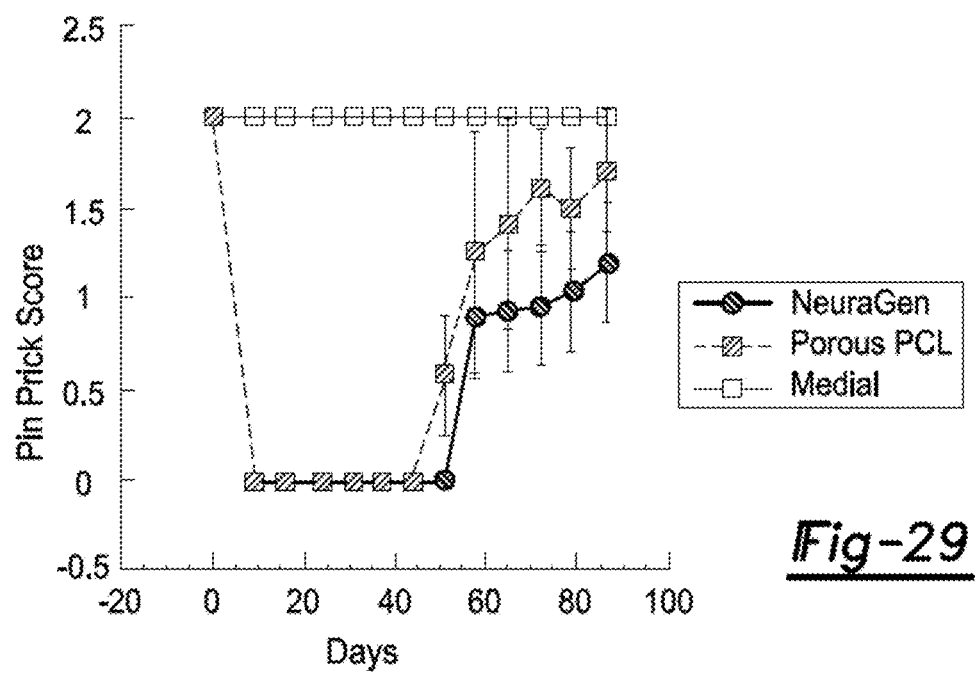
FIG. 29 shows pinprick scores after 7 weeks of implantation for comparative devices, including a PCL scaffold prepared in accordance with certain aspects of the present disclosure (N=3 rats/group) and a Neuragen™ nerve guide device (compared to a medial nerve). The rats having a porous PCL rats demonstrate earlier and accelerated sensory recovery compared to NeuraGen® implanted rats after injury.

In some experiments, rat survival is extended for 11 weeks post implantation. Rats are tested for sensory recovery. Nociceptive sensitivity (cutaneous innervation) is measured by applying a pinprick to the distal skin territory of the injured sciatic nerve (lateral hind paw). A score of 2 indicates a normal response and complete recovery. As a control, rats are tested on the medial side of the foot, innervated by the saphenous nerve, to confirm normal function. Pin Prick analysis reveals no sensory recovery for 6 weeks in either sciatic nerve implanted groups (score of 0; FIG. 29). However, rats with porous PCL scaffolds prepared in accordance with certain aspects of the present disclosure recover some nociceptive sensitivity at 7 weeks, whereas the rats with comparative NeuraGen® guides recover some nociceptive sensitivity later, at 8 weeks. Sensory recovery is accelerated in the PCL-porous group compared to NeuraGen® guide. These findings strongly support accelerated axon growth in the inventive porous PCL group compared with the comparative NeuraGen® devices. Thus, microchannel scaffold devices prepared in accordance with the present disclosure provide a greater potential for functional recovery and an overall improved approach over current standard of care in treating large gap peripheral nerve injury.

Example 5

Microchannel scaffold devices prepared in accordance with certain aspects of the present disclosure are further tested in a large animal model—the porcine model. After complete transection of the porcine sciatic nerve 5 cm rostral to the lateral femoral epicondyle, a 15 mm-long PCL device is implanted into the injury site. When examined 4 months later, the device integrated well with host tissue (FIGS. 30A-30D) and supported linear axonal regeneration over the gap; axons are observed in the distal stump of the nerve, 3.5 mm beyond the implant site (FIG. 30D). In FIG. 30A, arrows point to the suture where the device is anastomosed with the epineurium of the nerve stumps. FIGS. 30B-30C show axon labeling (NF200-green). In FIG. 30B, axonal penetration occurs into the device on the proximal side. These reach the distal side (FIG. 30C) of the device in a linear fashion. The interrupted lines demarcate host-scaffold interface. FIG. 30D shows associated axons and Schwann cells observed in the distal stump, 3.5 mm beyond the distal end of the implanted device. Thus, several regenerating axons are remyelinated by Schwann cells.

Reinnervation of sensory nerve tracts is observed upon stimulus of the skin on the lateral front part of the leg, much like the test results shown in FIGS. 24A-24B at three months. The pig is also capable of supporting itself on the leg with the implant. The hoof is deformed as the pig shifted its weight balance in the first few days to recovery, so it supports the leg with the implant on the hoof itself and not on the toes. This position is not changed even as the pig is recovering and functional regeneration regained. This procedure has been successfully completed in three pigs with similar results, including demonstrating sensory regeneration.

As such, the inventive technology can be used to achieve peripheral nerve repair after traumatic injury. The new tissue scaffold devices exhibit superiority to existing FDA-approved devices for treating longer gap injuries and more proximal, large gap injuries. When implanted in a subject, such tissue scaffolds have low levels of inflammation and immune system response in contrast with conventional devices. In addition, the inventive technology can be individualized to match the injury in each patient, among other advantages.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tissue scaffold for neural tissue growth comprising:
a porous sheath composed of a biocompatible and biodegradable material; and
an array composed of a plurality of microchannels each comprising a cylindrical shape with an inner diameter greater than 200 micrometers and a linear longitudinal axis, wherein the array is disposed within the sheath, wherein each microchannel of the plurality of microchannels comprises (i) a biocompatible and biodegradable material comprising a polyester polymer, and (ii) a porous wall comprising one or more pores, wherein each pore of the one or more pores comprises a diameter less than or equal to about 50 micrometers, and the porous wall comprises a thickness of less than or equal to about 100 micrometers, wherein one or more microchannels i) are treated with a biofunctional agent, ii) have different surface properties or surface roughness, iii) have surfaces with different moieties exposed, or iv) any combination thereof.

2. The tissue scaffold of claim 1, wherein the tissue scaffold has an open volume of greater than or equal to about 50 volume %.

3. The tissue scaffold of claim 1, wherein the tissue scaffold has an average open volume of greater than or equal to about 80 volume %.

4. The tissue scaffold of claim 1, wherein the porous wall has a thickness of greater than or equal to about 10 micrometers to less than or equal to about 70 micrometers, and a diameter of each microchannel is less than or equal to about 500 micrometers.

5. The tissue scaffold of claim 1, wherein the plurality of microchannels are closely packed within the sheath, so that a portion of each microchannel contacts another microchannel of the plurality.

6. The tissue scaffold of claim 1, wherein each microchannel of the plurality of microchannels has an oval or spherical cross-section and the plurality of microchannels are arranged within the sheath in a close-packed array.

7. The tissue scaffold of claim 1, wherein the polymer is selected from polycaprolactone, poly(lactic-co-glycolic acid) polymer, or a combination thereof.

8. The tissue scaffold of claim 1, wherein a microchannel density of the plurality of microchannels in the tissue scaffold is greater than or equal to about 1 to less than or equal to about 120 microchannels/mm$^2$ in the tissue scaffold.

9. The tissue scaffold of claim 8, wherein the microchannel density is greater than or equal to about 10 to less than or equal to about 30 microchannels/mm$^2$ in the tissue scaffold.

10. A tissue scaffold for neural tissue growth comprising:
a porous sheath composed of a biocompatible and biodegradable material having a first length; and
a plurality of microchannels disposed within the sheath defining a second length, wherein each microchannel of the plurality comprises (i) a biocompatible and biodegradable material comprising a polyester polymer, and (ii) a porous wall comprising one or more pores, wherein each pore of the one or more pores comprises a diameter less than or equal to about 50 micrometers, and the porous wall comprises a thickness of less than or equal to about 100 micrometers, wherein the first length is greater than the second length and the tissue scaffold has an open volume of greater than or equal to about 60 volume %, and wherein one or more microchannels of the plurality of microchannels are i) treated with a biofunctional agent, ii) have different surface properties or surface roughness, iii) have surfaces with different moieties exposed, or iv) any combination thereof.

11. The tissue scaffold of claim 10, wherein the porous sheath defines a first end and a second end, wherein the porous sheath extends at least about 1.5 mm past the first end and the second end and is configured to receive at least one suture.

12. The tissue scaffold of claim 10, wherein the biocompatible and biodegradable material is a first biocompatible and biodegradable material and the porous sheath is formed of a second biocompatible and biodegradable material distinct from the first biocompatible and biodegradable material.

13. The tissue scaffold of claim 10, wherein the biocompatible and biodegradable material of the porous sheath is polycaprolactone, poly(lactic-co-glycolic acid) polymer, or a combination thereof.

14. The tissue scaffold of claim 10, wherein the plurality of microchannels are closely packed within the sheath, so that a portion of each microchannel contacts another microchannel of the plurality.

15. The tissue scaffold of claim 10, wherein a microchannel density of the plurality of microchannels in the tissue scaffold is greater than or equal to about I to less than or equal to about 120 microchannels/mm$^2$ in the tissue scaffold.

16. The tissue scaffold of claim 10, wherein the biofunctional agent is selected from fibronectin, laminin, collagen, or a combination thereof.

17. The tissue scaffold of claim 10, wherein the porous sheath comprises pores less than or equal to about 10 micrometers in diameter.

18. The tissue scaffold of claim 10, wherein the scaffold has an elastic modulus of about 1.1 MPa.

19. The tissue scaffold of claim 10, wherein the porous sheath comprises a porosity of about 80%.

20. A system for facilitating regrowth of nerve tissue, the system comprising: the tissue scaffold of claim 10, wherein the tissue scaffold of claim 10 further
comprises a proximal end and a distal end, wherein the plurality of microchannels comprise fibronectin;
a plurality of axons positioned within the plurality of microchannels, wherein a density of the axons is greater at the proximal end then the distal end, wherein the axons extend in a direction approximately parallel to the length of the microchannels; and
a plurality of Schwann cells in contact with at least a portion of the axons, wherein the system is in vivo.

21. The tissue scaffold of claim 1, wherein the porous wall comprises a porosity of about 70%.

22. The tissue scaffold of claim 1, wherein the cylindrical shape maintains a constant inner diameter across the linear longitudinal axis.

23. The tissue scaffold of claim 1, wherein each of the plurality of microchannels comprises an inner surface configured to receive neural or axonal tissue.

* * * * *